(12) United States Patent
Mitra et al.

(10) Patent No.: US 8,409,154 B2
(45) Date of Patent: *Apr. 2, 2013

(54) METHOD OF DELIVERING A SKIN BENEFIT

(75) Inventors: Shekhar Mitra, Indian Hill, OH (US); Dean A. Zimmerman, West Chester, OH (US); Vincent York-Leung Wong, Hamilton, OH (US); Marina Belkin, West Chester, OH (US)

(73) Assignee: Wyeth, Madison, NJ (US)

(*) Notice: Subject to any disclaimer, the term of this patent is extended or adjusted under 35 U.S.C. 154(b) by 639 days.

This patent is subject to a terminal disclaimer.

(21) Appl. No.: 12/465,333

(22) Filed: May 13, 2009

(65) Prior Publication Data

US 2009/0287168 A1 Nov. 19, 2009

Related U.S. Application Data

(60) Provisional application No. 61/093,049, filed on Aug. 29, 2008, provisional application No. 61/093,009, filed on Aug. 29, 2008, provisional application No. 61/053,480, filed on May 15, 2008.

(51) Int. Cl.
*A61M 35/00* (2006.01)
*A61H 33/06* (2006.01)

(52) U.S. Cl. .............. 604/290; 4/537; 4/535; 132/200

(58) Field of Classification Search .............. 604/290; 132/200; 4/535
See application file for complete search history.

(56) References Cited

U.S. PATENT DOCUMENTS

| | | | |
|---|---|---|---|
| 2,995,521 A | 8/1961 | Estignard-Bluard | |
| 3,298,368 A * | 1/1967 | Charos | 604/291 |
| 3,541,581 A | 11/1970 | Monson | |
| 4,087,675 A * | 5/1978 | Sansonetti | 604/292 |
| 4,405,489 A | 9/1983 | Sisbarro | |
| 4,528,111 A | 7/1985 | Su | |
| 4,649,895 A | 3/1987 | Yasuki et al. | |
| 4,651,503 A | 3/1987 | Anderson, III et al. | |
| 5,026,542 A | 6/1991 | Baines et al. | |
| 5,143,722 A | 9/1992 | Hollenberg et al. | |
| 5,248,495 A | 9/1993 | Patterson et al. | |
| 5,308,643 A | 5/1994 | Osipow et al. | |
| 5,326,556 A | 7/1994 | Barnet et al. | |
| 5,500,211 A | 3/1996 | George et al. | |
| 5,891,116 A * | 4/1999 | Mast | 604/290 |
| 5,918,590 A | 7/1999 | Burkett et al. | |

(Continued)

FOREIGN PATENT DOCUMENTS

| | | |
|---|---|---|
| EP | 1 090 614 | 4/2001 |
| EP | 1 181 911 | 2/2002 |

(Continued)

OTHER PUBLICATIONS

Emmerson, "Men: how to shave your face without the irritation", May 5, 2006, www.associatedcontent.com.*

(Continued)

*Primary Examiner* — Susan Su
(74) *Attorney, Agent, or Firm* — K&L Gates LLP

(57) ABSTRACT

A method of providing a skin benefit to the skin including the use of a skin care active and a portable moist heat delivery system comprising: a water vapor generating portion comprising a water vapor source and a heat source; and a water vapor-air regulating portion located at a skin-facing side of the water vapor generating portion, the water vapor-air regulating portion comprising a water vapor-air mixing layer, a water vapor-air distribution layer, a latent heat delivery surface, and optionally a skin contact layer, where the water vapor generating portion and the water vapor-air regulating portion are in fluid communication is disclosed.

21 Claims, 5 Drawing Sheets

U.S. PATENT DOCUMENTS

| | | | |
|---|---|---|---|
| 5,984,995 A | 11/1999 | White | |
| 6,099,556 A | 8/2000 | Usui | |
| 6,245,347 B1 * | 6/2001 | Zhang et al. | 424/449 |
| 6,303,142 B1 * | 10/2001 | Zhang et al. | 424/449 |
| 6,409,746 B1 * | 6/2002 | Igaki et al. | 607/109 |
| 6,629,964 B1 * | 10/2003 | Ono et al. | 604/304 |
| 6,824,557 B2 * | 11/2004 | Tone et al. | 607/114 |
| 7,021,848 B1 * | 4/2006 | Gruenbacher et al. | 401/1 |
| 7,166,279 B2 | 1/2007 | Law | |
| 2004/0175347 A1 | 9/2004 | Bissett | |
| 2005/0192653 A1 | 9/2005 | Tsunakawa et al. | |
| 2005/0196424 A1 * | 9/2005 | Chappa | 424/423 |
| 2006/0228319 A1 | 10/2006 | Vona, Jr. et al. | |
| 2006/0229691 A1 * | 10/2006 | Noskov et al. | 607/96 |
| 2006/0275237 A1 | 12/2006 | Bissett et al. | |
| 2006/0276863 A1 * | 12/2006 | Kumamoto et al. | 607/96 |
| 2007/0068508 A1 | 3/2007 | York-Leung Wong | |
| 2007/0196311 A1 * | 8/2007 | Gross | 424/70.13 |
| 2008/0312579 A1 * | 12/2008 | Chang et al. | 604/20 |
| 2009/0019634 A1 * | 1/2009 | Lipponen | 4/524 |
| 2009/0062890 A1 * | 3/2009 | Ugajin et al. | 607/104 |
| 2009/0112231 A1 | 4/2009 | Luizzi | |
| 2009/0283106 A1 | 11/2009 | Torgerson et al. | |
| 2009/0287280 A1 | 11/2009 | Wong et al. | |
| 2010/0010598 A1 * | 1/2010 | Igaki et al. | 607/109 |

FOREIGN PATENT DOCUMENTS

| | | |
|---|---|---|
| WO | WO 99/51174 | 10/1999 |
| WO | WO 2006/013988 | 2/2006 |
| WO | WO 2008/116084 | 9/2008 |

OTHER PUBLICATIONS

International Search Report from the European Patent Office for PCT Application PCT/US2009/043765 filed May 13, 2009, mailed Oct. 19, 2009.

* cited by examiner

METHOD OF DELIVERING A SKIN BENEFIT

CROSS REFERENCE TO RELATED APPLICATIONS

This application claims the benefit of U.S. Provisional Application No. 61/053,480, filed May 15, 2008; U.S. Provisional Application No. 61/093,009, filed Aug. 29, 2008; and U.S. Provisional Application No. 61/093,049, filed Aug. 29, 2008.

FIELD OF THE INVENTION

The present invention is directed to method of providing a skin benefit by the use of a portable moist heat delivery system and a skin care active. In particular, the present invention is directed to applying a skin care composition containing a skin care active to the skin, and then applying a portable moist heat delivery system that generates water vapor and provides moist heat to the skin.

BACKGROUND OF THE INVENTION

A variety of approaches have been developed to deliver skin care actives to the skin. A common method of providing a skin care active is through the use of skin care compositions containing actives such as actives to regulate and/or improve skin conditions. Additionally, traditional methods of prepping the skin for treatment such applying a composition or shaving the skin include the use of applying a hot towel. However, hot, wet towels are either difficult and inconvenient to use, or do not provide moist heat of a consistent temperature for a length of time sufficient to deliver a skin benefit.

Disposable heat wraps have become a popular way of applying heat to relieve discomfort of temporary or chronic body aches and pains. Disposable heat wraps typically comprise an exothermic composition for generating heat, wherein the exothermic composition typically comprises metal powder, salts, and water that allows the exothermic composition to release heat upon oxidation of the metal powder. Other disposable or reusable devices can use energy produced by neutralization of acids and bases; heat of hydration of inorganic salts; re-heatable gels; and electrical energy to produce heat. Such devices usually produce heat but contain little moisture.

Based on the foregoing, there is a need for a moist heat source which is easy and convenient to use with a skin care active, and which also provides a consistent temperature and moisture to the skin for a length of time sufficient to deliver a benefit to the skin.

None of the existing art provides all of the advantages and benefits of the present invention.

SUMMARY OF THE INVENTION

A method of providing benefits to the skin comprising: i) applying a skin care composition to the skin, ii) providing a portable moist heat delivery system comprising a water vapor generating portion comprising a water vapor source and a heat source; and a water vapor-air regulating portion located at a skin-facing side of the water vapor generating portion, the water vapor-air regulating portion comprising a water vapor-air mixing layer, a water vapor-air distribution layer, and optionally a skin contact layer; iii) the water vapor generating portion and the water vapor-air regulating portion being in fluid communication; and the water vapor-air regulating portion having a latent heat delivery system disposed adjacent the water vapor-air regulating portion and wherein the portable moist heat delivery system transfers from about 15% to about 95% of heat to a user as latent heat of condensation, while maintaining skin temperature less than about 43° C.

A method of providing a benefit to the skin comprising: i) providing a portable moist heat delivery system comprising a steam generating portion comprising a steam source and a heat source; and a dew point reduction portion located at a skin-facing side of the steam generating portion, the dew point reduction portion comprising a vapor-air mixing layer, a vapor-air distribution layer, and optionally a skin contact layer, the steam generating portion and the dew point reduction portion being in fluid communication and the steam regulating portion having a latent heat delivery system disposed adjacent the steam-air regulating portion and; ii) applying the portable moist heat delivery system to the skin of a user; iii) initiating heating of the portable moist heat delivery system; and iv) supplying a vapor-air mixture generated by the portable moist heat delivery system to the skin of the user; wherein the vapor-air mixture provides latent heat, resulting in skin benefit within about 1 minute to about eight hours from the initiation of heating of the portable moist heat delivery system; and wherein skin temperature is maintained below about 43° C.; and wherein a skin care active is incorporated into the steam-generating portion, into the steam source, or into the dew point reduction portion.

A method of providing benefits to the skin comprising: i) applying a portable moist heat delivery system to the facial skin, wherein the portable moist heat delivery system comprises: ii) a water vapor generating portion comprising a water vapor source and a heat source; and iii) a water vapor-air regulating portion located at a skin-facing side of the water vapor generating portion, the water vapor-air regulating portion comprising a water vapor-air mixing layer, a water vapor-air distribution layer, and optionally a skin contact layer; the water vapor generating portion and the water vapor-air regulating portion being in fluid communication; and the water vapor-air regulating portion having a latent heat delivery system disposed adjacent the water vapor-air regulating portion and wherein the portable moist heat delivery system transfers from about 15% to about 95% of heat to a user as latent heat of condensation, while maintaining skin temperature less than about 43° C.; iv) applying a shaving composition to the facial skin; and v) shaving the facial skin.

BRIEF DESCRIPTION OF THE DRAWING FIGURES

DETAILED DESCRIPTION OF THE INVENTION

Figure 1:
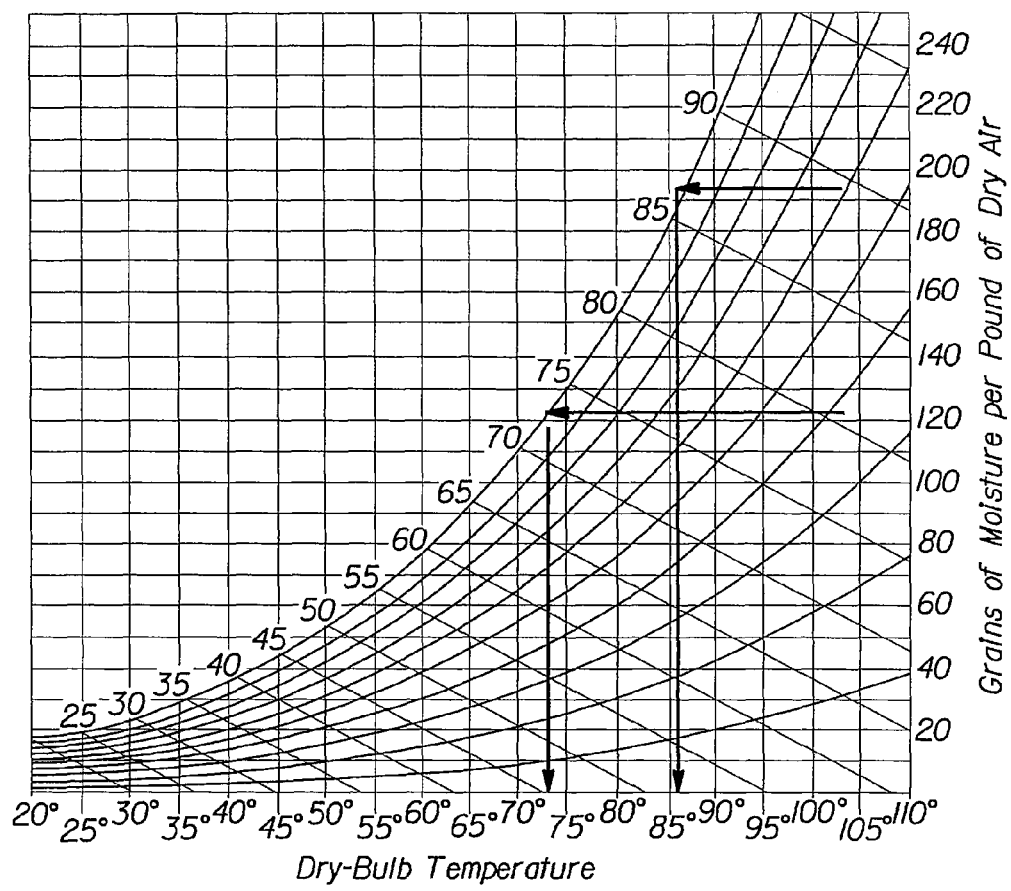
FIG. 1 is a psychrometric chart illustrating humidity ratio relationship to dew point and energy content of a water vapor and air mixture.

The method of delivering a skin benefit of the present invention includes regulating the skin condition by i) applying to the skin a skin care composition comprising a skin care active, and ii) applying to the skin a portable moist heat delivery system of the present invention. The heat delivery system can be a single-use disposable system or can be incorporated into a reusable or partially reusable system. It is believed that the moist heat delivered by portable moist heat delivery system acts to enhance the penetration of the beneficial skin actives. The portable moist heat delivery system of the present invention delivers a moist heat which can be applied to the skin for a length of time up to about eight hours. This heat does not exceed a temperature which would burn the skin.

The invention can comprise, consist of, or consist essentially of the elements and limitations of the invention described herein, as well as any of the additional or optional ingredients, components, or limitations described herein.

As used herein, "water vapor" refers to water in the gaseous state. "Water vapor-air mixture" and "water vapor-air mixing" refer to adding air to "water vapor" as defined herein. The energy added to accomplish the phase change from liquid water to water vapor is latent heat of evaporation. The latent heat of evaporation energy is released upon the phase change of condensation of water vapor to liquid water and referred to as latent heat of condensation. The word "steam" as used herein also refers to water in the gaseous state and differs from the term "water vapor" in that steam refers only to water vapor and not a mixture of water vapor and liquid water droplets.

As used herein "dew point" temperature refers to the temperature to which a water vapor-air mixture must cool before water therein begins to condense.

"Humidity ratio" is the ratio of the weight of water vapor to the weight of dry air.

"Latent heat", as used herein refers to the amount of energy in the form of heat released or absorbed by a substance during a change of phase (i.e. to or from solid, liquid, or gas).

"Moisture", as used herein refers to water.

"Moist heat", as used herein, refers to heat wherein about 15% to about 95% of the transferable heat energy is in the form of latent heat of condensation of water vapor. As water vapor and water vapor condensation are associated with moist heat, moist heat includes a moisture component. The moist heat delivery system may also transfer water vapor and, when condensation occurs and latent heat released, liquid water.

A "pre-selected temperature", as used herein, may include the stated temperature plus or minus 1° C. or alternatively plus or minus 2° C.

The term "median particle size" means that there are approximately as many particles that have a size larger than the designated median size as there are particles that have a size smaller than the designated median size.

Other definitions are provided as necessary as they occur within the description of the invention.

All caliper-measured thicknesses disclosed herein are measured according to ASTM Method No. D5729, unless otherwise specified.

All basis weights disclosed herein are measured according to ASTM Method No. D3776, unless otherwise specified.

All air-permeabilities disclosed herein are measured according to ASTM Method No. D737, unless otherwise specified.

All moisture vapor transmission rates (MVTR) disclosed herein are measured according to ASTM Method No. E96 unless otherwise specified.

As used herein "Skin care actives," or "actives," means compounds that, when applied to the skin, provide a benefit or improvement to the skin. Skin care actives may be used for regulating and improving skin condition. It is to be understood that skin care actives are useful not only for application to skin, but also to hair, nails, and other mammalian keratinous tissue.

As used herein "Beauty Care Benefit" means a cosmetic benefit resulting from the application of a skin care active for cleansing, beautifying, promoting attractiveness or altering appearance for application on human keratinous tissue (including skin, hair and nails) with the intent to enhance the appearance of such tissue, and not intended for use as a drug.

As used herein "Regulating skin condition" means providing a beauty care benefit by maintaining skin appearance and/or feel with little to no degradation in appearance and/or feel. "Improving skin condition" means providing a beauty care benefit by affecting a positive change in skin appearance and/or feel. The skin appearance and/or feel benefit may be a chronic benefit and may include one or more of the following: thickening of keratinous tissue (e.g., building the epidermis and/or dermis and/or sub-dermal layers of the skin, and where applicable the keratinous layers of the nail and hair shaft, to reduce skin, hair, or nail atrophy); increasing the convolution of the dermal-epidermal border (also known as the rete ridges); preventing loss of skin or hair elasticity, for example, due to loss, damage and/or inactivation of functional skin elastin, resulting in such conditions as elastosis, sagging, loss of skin or hair recoil from deformation; reduction in cellulite; change in coloration to the skin, hair, or nails, for example, under-eye circles, blotchiness (e.g., uneven red coloration due to, for example, rosacea), sallowness, discoloration caused by hyperpigmentation, maintaining/improving the signs of skin aging, and maintaining/improving insult-affected keratinous tissue.

"Insult-affected keratinous tissue," means keratinous tissue which exhibits discomfort, irritation, an unpleasant or irregular appearance, and the like, for example after exposure to a physical and/or chemical irritant. Non-limiting examples of insult-affected keratinous tissue include burn (e.g., sunburns, windburn, chemical or thermal burns); rashes (e.g., diaper rash, shaving rash and allergen-induced rashes); discoloration (e.g., bleaching, staining, hyperpigmentation); nicks and cuts (e.g., shaving insults); and dry, chapped or rough skin (e.g., due to exposure to example wind, cold and/or low humidity). Non-limiting examples of insults include radiation, wind, low humidity, allergens, pollutants, chemical and natural irritants, bodily fluids, bodily waste, excessive moisture, bacteria, fungi, etc.

As used herein "signs of skin aging," include, but are not limited to, all outward visibly and tactilely perceptible manifestations, as well as any macro- or micro-effects, due to keratinous tissue aging. These signs may result from processes which include, but are not limited to, the development of textural discontinuities such as wrinkles and coarse deep wrinkles, fine lines, skin lines, crevices, bumps, large pores, unevenness or roughness; loss of skin elasticity; discoloration (including undereye circles); blotchiness; sallowness; hyperpigmented skin regions such as age spots and freckles; keratoses; abnormal differentiation; hyperkeratinization; elastosis; collagen breakdown, and other histological changes in the stratum corneum, dermis, epidermis, vascular system (e.g., telangiectasia or spider vessels), and underlying tissues (e.g., fat and/or muscle), especially those proximate to the skin.

In all embodiments of the present invention, all percentages are by weight of the total composition, unless specifically stated otherwise. All ratios are weight ratios, unless specifically stated otherwise. All ranges are inclusive and combinable; therefore, every range given throughout this specification will include every narrower range that falls within such broader range as if such narrower ranges were all expressly written herein. The number of significant digits conveys neither a limitation on the indicated amounts nor on the accuracy of the measurements. Unless explicitly stated otherwise, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

Portable Moist Heat Delivery System

The benefits of moist heat, such as increasing penetration of the skin care actives, can only be achieved if a moist heat device delivers a particular, effective amount of moist heat. In order to deliver an effective amount of moist heat, the portable moist heat delivery system of the present invention includes a water vapor generating portion comprising a water vapor source and a heat source; and a water vapor-air regulating portion located at a skin-facing side of the water vapor generating portion, the water vapor-air regulating portion comprising a water vapor-air mixing layer, a water vapor-air distribution layer, and optionally a skin contact layer; the water vapor generating portion and the water vapor-air regulating portion being in fluid communication and the water vapor-air regulating portion having a latent heat delivery system disposed adjacent the water vapor-air regulating portion which delivers moist heat at a pre-selected temperature range. Specifically, the structure is designed to provide water vapor and air mixing and distribution to provide rapid, safe, efficient and sustained moist heat production and transfer. Embodiments of the portable moist heat delivery system are described in detail in copending U.S. application Ser. No. 12/454,129 entitled "Portable Moist Heat System", filed on May 13, 2009.

In one embodiment, the water vapor generating portion generates water vapor which is at a temperature of from about 50° C. to about 70° C. As the water vapor is formed not only is the water vapor warmed but also heat is stored as latent heat of vaporization. In order to generate water vapor, the water vapor source, must heat quickly and deliver a high water vaporization rate for a period of time of at least about 10 minutes and preferably about 30 minutes or more. The stored heat of vaporization is released when the water vapor condenses. Water vapor is an ideal candidate to transfer heat because of the magnitude of heat transfer by latent heat when it condenses, and because water vapor is easily generated and available. In exemplary embodiments described herein, heat for generating the water vapor is generated using an exothermic thermal composition such as for example an iron based thermal composition as disclosed in U.S. application Ser. No. 11/233,916. However, as one skilled in the art will appreciate, other thermal materials compositions and/or sources of heat and/or other energy sources may likewise be used to generate heat in the practice of the invention.

In an exemplary embodiment, the water vapor generating portion includes a thermal composition for generating heat and water available for vaporization. Optionally, these components may be intermixed.

The water vapor-air regulating portion of the moist heat system has multiple purposes and functions. The first function of which is to allow sufficient air to enter the water vapor generating portion to support the exothermic reaction. Providing sufficient air to support the exothermic reaction is important because the permeable portion of the portable moist heat delivery system is worn against the skin. To vaporize the water in the exothermic composition, the temperature of the composition can be as high as about 70° C. However, because human skin can burn at temperatures of about 43° C. or higher, it must be protected from the hot exothermic composition. Thus, in the present system, as water vapor is generated, it exits the water vapor generating portion through/into the water vapor-air regulating portion. As the water vapor passes through the water vapor-air regulating portion, the water vapor is mixed with air and distributed such that the dew point temperature of the vapor-air mixture is lowered to about 43° C., a temperature which will not burn the skin. Thus, the water vapor-air regulating portion also safeguards the skin against the high temperature of the water vapor generated in the water vapor generating portion. This also protects the skin from heat damage.

Previously it was thought that the temperature of the water vapor exiting a moist heat device must be lowered to less than about 50° C. in order to prevent skin burns. However it has been found that it is not only or primarily the temperature of the water vapor that is important for preventing burns, but rather the energy content of the exiting water vapor and its ability to transfer energy to the skin is important.

However, it should be recognized that contact with the skin or hair with a high temperature source will result in a burn only if the skin is unable to dissipate energy it receives. Thus, energy transfer as well as temperature is determinative of the potential for damage. Typically, in dry or conductive heat transfer a burn occurs when the skin temperature exceeds about 43° C. However, without wishing to be held to any theory, it is believed that in the case of moist heat, much of the energy is transferred via latent heat of condensation. Thus, even though the temperature of water vapor-air mix may be higher, e.g., about 50° C., the skin will not burn if the amount of energy transferred by the water vapor is insufficient and/or transferred at a rate insufficient to elevate the skin temperature above 43° C. and/or dissipated at a rate sufficient to maintain the skin temperature at about 43° C. or less.

Thus, the system of the present disclosure enables one to use temperatures higher than about 43° C. without harm to human skin or hair. Previously, it was believed that the temperature per se of the water vapor exiting a moist heat device must be lowered to less than about 50° C. as measured by a dry bulb thermometer or thermocouple in order to prevent burns. However, the potential for tissue damage and/or energy transfer is not reliably reflected in the temperature as measured by conventional dry bulb or thermocouple, but rather is more reliably related to the dew point temperature of the water vapor. Unlike the dry bulb temperature, the dew point temperature is related to the amount of water vapor in the gas mixture. With the portable moist heat delivery device of the present invention the skin is contacted with water vapor which causes the water vapor to condense and release its latent heat via condensation. With such a mode of heat transfer, the condensation of the water vapor releases a high quantity of energy at a fast rate. Thus, to prevent skin burn, it is important to control the condensing temperature of the water vapor-air mixture, and not merely the dry bulb temperature of the water vapor-air mixture. The condensing temperature of the water vapor-air mixture is its dew point temperature.

As shown in the psychrometric chart of FIG. 1, dew point temperature is determined by the humidity ratio of the water vapor-air mixture which is the absolute level of moisture in the air. The relationship of dew point temperature and humidity ratio is that dew point temperature increases as the humidity ratio increases. The energy content of a water vapor-air mixture is more impacted by the amount of water vapor (i.e. stored latent heat) than by its dry bulb temperature (i.e., sensible heat). In order to avoid skin burn, the amount or ratio of water vapor to dry air must be regulated so that the water vapor condenses at a temperature that is less than about 43° C. In regulating the water vapor-air ratio, there may be an incidental decrease in the dry bulb temperature of the water vapor-air mixture. However, regulating the dry bulb temperature of the water vapor-air mixture is not required because the energy gained or lost in a temperature change is significantly less than the energy present as latent heat. Thus, the amount of energy transferred via latent heat can be controlled by regulating the water vapor to dry air ratio. Such a ratio can be expressed as pounds of water vapor/pound of dry air or as kg of water vapor/kg dry air.

Figure 2:
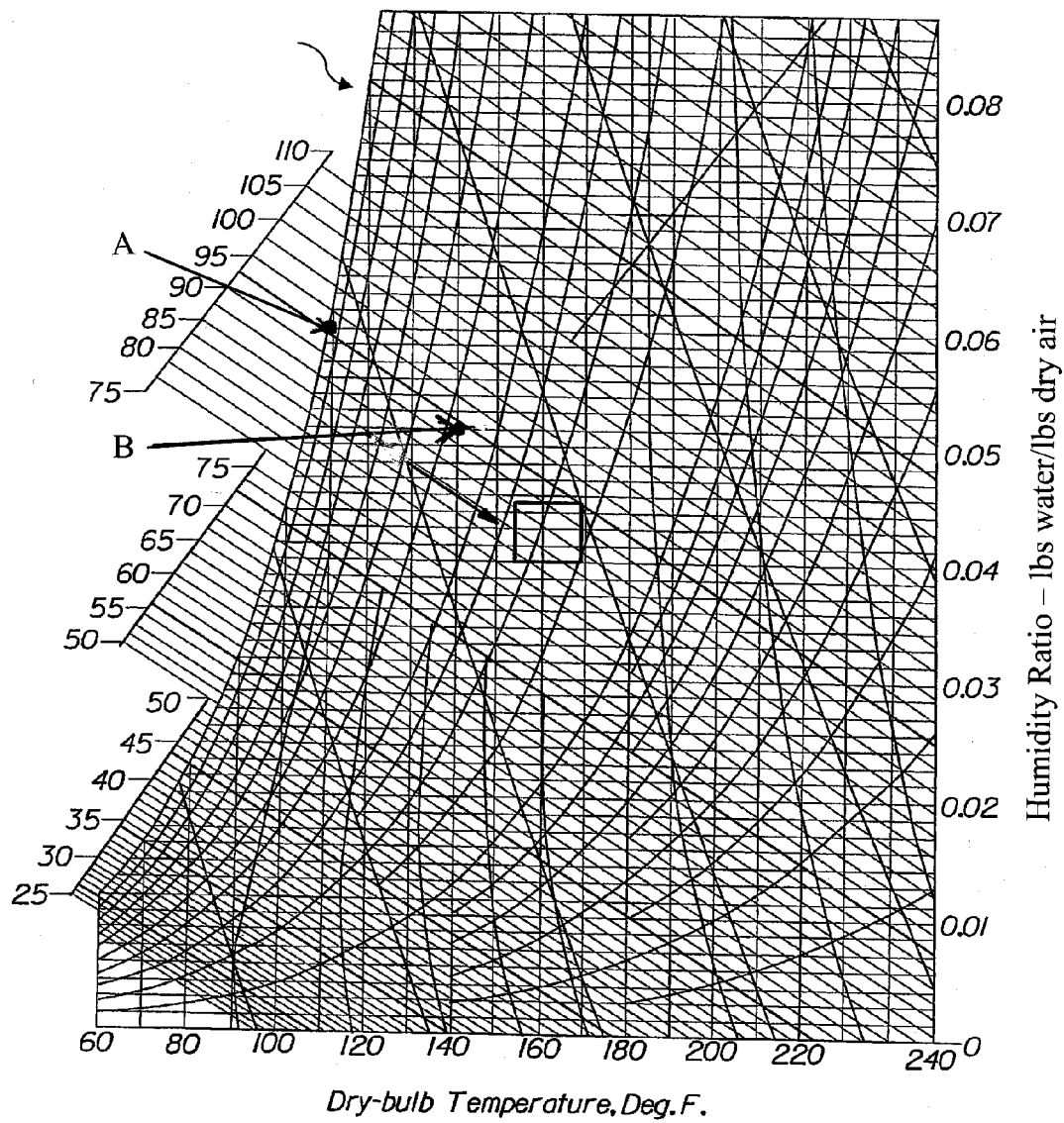
FIG. 2 is a psychrometric chart illustrating dry bulb temperature and dew point temperature.

As can be seen in the psychrometric chart of FIG. 2, point A represents a water vapor-air mixture at its saturation point and has a dew point temperature of about 43.3° C. (about 110° F.). The water vapor-air ratio at point A is about 0.06 kg water vapor/kg dry air.

Point B represents a lower humidity, or less saturated, water vapor-air mixture at a water vapor-air ratio of about 0.052 kg water/kg dry air. To have the same energy content as the water vapor-air mixture of Point A, the water vapor-air mixture at Point B has a dry bulb temperature of about 60° C. (about 140° F.). When a water vapor-air mixture such as that at Point B condenses on the skin, it will condense at about 40.6° C. (about 105° F.). As it condenses, the energy transfer rate will be very high but will not burn the skin even though its dry bulb temperature is about 60° C. (about 140° F.), since its condensing temperature or dew point is only about 40.6° C. In contrast, when a water vapor-air mixture at Point A condenses on the skin, it will condense at about 43.3° C. (about 110° F.) and rapidly transfer its latent heat content, posing a great risk of burn even though its dry bulb temperature is significantly less that that of the water vapor-air mixture at Point B.

Thus, unlike the prior art, the moist heat delivery system in the present invention avoids skin burns by regulating the water vapor-air mixture ratio as opposed to regulating the dry bulb temperature of a water vapor-air mixture. By regulating the water vapor-air ratio to less than about 0.065 kg water/kg dry air, and alternatively to less than about 0.060 kg water/kg dry air, the dew point temperature of the water vapor-air mixture will be less than about 43° C. One of the advantages in controlling the dew point temperature of the moist heat delivery system is that the thermodynamics of the system provides a temperature modulation wherein the transfer of latent heat is modulated by the skin temperature (i.e. the latent heat is transferred at the dew point. Thus, transfer will not occur unless the skin temperature is at or below the dew point of the water vapor).

The portable moist heat delivery systems described herein selectively direct water vapor against a user's skin at the desired dew point temperature of from about 36° C. to about 50° C., alternatively from about 36° C. to about 45° C., alternatively from about 36° C. to about 42° C., and alternatively from about 38° C. to about 40° C. The system can direct water vapor to the skin for a period of from about twenty seconds to about eight (8) hours, alternatively from about twenty minutes to about four (4) hours, alternatively from about one (1) minute to about sixty (60) minutes, alternatively from about fifteen (15) minutes to about thirty (30) minutes, alternatively from about one (1) minute to about twenty (20) minutes, alternatively from about twenty (20) minutes to about forty (40) minutes and alternatively from about one half (½) hour to about two (2) hours. The maximum skin temperature and the length of time of maintaining the skin temperature at the maximum skin temperature may be appropriately selected by a person needing such treatment such that the desired benefits are achieved without any adverse events such as skin burns. The water vapor-air regulating portion ensures that an amount of moist heat is delivered to a user's skin without adverse effects.

The water vapor-air regulating portion of the moist heat system has a water vapor air mixing layer and a water vapor air distribution layer. Further, as a function of the water vapor-air regulator is to adjust the proportion of water vapor to air, the water vapor-air regulating portion must be in fluid communication with the water vapor generation portion with water vapor passing freely between the water vapor air generation portion and the water vapor-air regulator portion. In an exemplary embodiment, the water vapor-air regulation portion is adjacent the water vapor generation portion. Additionally, the water vapor-air regulating portion needs a supply of air to accomplish the water vapor-air ratio adjustment but as a specific ratio or ratio range is desired regulation of the air supply is desirable. Air supply may be regulated, for example, by control of the density and/or porosity of the materials used to construct the system or, alternatively, by the use of channels and apertures in water and/or air impermeable materials.

The interface between the water vapor-air regulating portion and end user is the latent heat delivery surface proximate the skin and optionally a skin contact layer. In some embodiments that latent heat delivery surface and/or skin contact layer may contact or partially contact the skin. In other embodiments, it may be desirable to have a small air gap between the latent heat delivery surface and/or skin contact layer and the skin. In the moist heat delivery system the generated water vapor is preferentially directed toward the latent heat delivery surface. The water-vapor may be passed though the latent heat delivery surface to the skin, water-vapor may condense at the latent heat delivery surface/skin contact layer transferring the latent heat energy to the user or, alternatively, a combination of water vapor condensation and water-vapor transfer may occur.

The terminology of latent heat delivery "surface" has been selected. However, surface is not intended to be limited to any particular geometric shape, and includes, but is not limited to, planar surfaces, contoured surfaces, and irregular surfaces. The latent heat transfer surface may comprise a layer of material. Optionally, the latent heat delivery surface may be integrally attached to the water vapor-air regulator portion, and/or a surface of a portion of the water vapor-air regulator portion. Alternatively the latent heat delivery surface may be a part of a reusable holder for the system, for example. In those embodiments including a hair contact layer, the latent heat delivery surface may be in contact with the skin contact layer.

Water Vapor Generating Portion

The water vapor generating portion of the present invention contains at least one water vapor source and a heat source. The water vapor source can generate energy and water vapor in any number of ways. Non-limiting examples of heat sources include by chemical energy; energy produced by neutralization of acids and bases; heat of hydration of inorganic salts; reheatable gels; and electrical energy. Water vapor sources can be combined with the heat source. For example an exothermic heat cell can include a mixture of fuel (i.e., the heat source) and water and/or water held in a water manager (such as a gel) as the water vapor generating portion of the moist heat delivery system. Alternatively, the water and heat source can be separated with the water being supplied from a reservoir or applied to a surface, such as the hair, and then contacted with the heat produced by the heat generating source. In water vapor generating portions that comprise energy sources that are not compatible with water, for example an electrical element, the energy source can be used to heat separate water-containing elements to produce water vapor. A non-limiting example of a water vapor generating portion useful in the present invention uses an exothermic composition including water in a water manager formed in at least one water vapor generating heat cell. The moist heat delivery system may contain a single heat cell or a plurality of heat cells. In certain embodiments, a plurality of heat cells is particularly useful in the system of the present invention. A plurality of heat cells allows for flexible systems of various size and shape. In addition, the use of a plurality of heat cells may allow for an easy control of the water vapor-air mixing ratio for controlling the dew point. For example, the dew point temperature for a fixed water-vapor mixing and aeration design can be increased/decreased by increasing/decreasing the number of heat cells. Further, the duration of heating and total energy delivered can be controlled by varying the number of heat cells used per unit area of vapor generating portion. The greater the number of heat cells per area, the longer the duration of heating provided. The fewer number of heat cells per area, the shorter the duration of heat provided. In certain embodiments, it may be desirable to use a combination of a moist heat delivery system, such as described herein, and one or more other types of heat cells, such as dry heat cells.

Exothermic Composition

In one exemplary embodiment, the thermal energy for generation of water vapor is provided by an exothermic heat cell comprising a particulate exothermic composition. The exothermic composition may comprise a flowable particulate pre-mix and a brine solution. The exothermic compositions disclosed in U.S. application Ser. No. 11/233,916 may be suitable in certain embodiments.

Particulate exothermic compositions have both desirable features and certain considerations that must be addressed to achieve the desirable features. For example, the performance of an exothermic heat cell can be impacted by the particle size of the particulate components of the exothermic composition in two main ways. First, variation in particle size of the particulate components of an exothermic composition can lead to particle separation or segregation within an exothermic composition. Particle size directly affects particle mobility and particulate components can vary in their mobility, resulting in particle separation or segregation. Changes in the exothermic composition due to particle segregation can lead to less than optimal or desired reaction behavior.

The exothermic compositions defined herein comprise particulate components having defined median particle size ranges such that the exothermic compositions resist particle separation or segregation. It is contemplated, however, that particulate components having median particle size ranges above or below the ranges defined herein are suitable for use in the exothermic compositions defined herein.

The second way that performance of exothermic heat cells can be impacted by the particle size of the particulate components of the exothermic composition is that particle size affects accessibility of air through the particulate exothermic composition. In order to support and sustain a vigorous exothermic reaction for releasing water vapor, the particulate exothermic composition should be porous in order to allow free access of air to the reactants of the particulate exothermic composition. The particulate exothermic composition should be porous even with initially high water content (for high water vapor generation) and remain porous throughout the reaction. To be and remain porous, the particulate exothermic composition needs to have an efficient water manager component and the particle sizes of the components of the exothermic composition should exhibit loose particle packing behavior. Without wishing to be bound by any theory, it is believed that proper porosity and maintaining porosity is an important factor in creating heat cells that have long periods of heat production (such as up to 24 hours) and in creating a composition that has a consistent, reproducible behavior in a plurality of heat cells.

In one embodiment, the heat cells of the present disclosure may comprise a particulate exothermic composition that provides for reliable heating and accordingly reliable and substantial water vapor generation over time frames of a few minutes to hours when the heat cells are incorporated into portable moist heat delivery systems. The exemplary particulate exothermic composition comprises a particulate pre-mix composition and a brine solution. Components of the particulate premix composition include iron powder, carbon, absorbent gelling material, and water, which components are described in detail hereinafter. Components of the brine solution include a metal salt, water, and optionally a hydrogen gas inhibitor such as sodium thiosulfate. The particulate exothermic compositions defined herein are generally prepared by constructing the particulate premix composition and rapidly dosing the premix with the brine solution to result in the formation of the exothermic composition.

For use in a moist heat device a particulate exothermic composition should have the ability to provide fast initial heating and also provide heat for a sustained period of time. Typical exothermic heat devices known in the art generally can either provide high levels of heat rapidly but last only a few minutes, or they can provide heat for a sustained period of time, but can take up to about 30 minutes to heat. The present invention provides both rapid and sustained heating achieved in part by the choice of components within the particulate exothermic composition. By way of non-limiting example, by modifying component particle size, the speed of heating, duration of heating and temperature of the exothermic reaction can be controlled.

By way of illustration, one particular method of modifying the exothermic reaction involves using iron powder having a median particle size of about 200 µm and an absorbent gelling material having a median particle size of about 300 µm, wherein the median particle size ratio of absorbent gelling material to iron powder is about 1.5:1. This particular ratio of absorbent gelling material to iron powder provides for an exothermic composition that exhibits rapid initial heating and water vapor generation, which has been difficult to achieve with conventional exothermic compositions. It is believed that attempts to incorporate a high level of moisture in conventional exothermic compositions results in water in the interstitial particle voids which restricts oxygen flow and slows the rate of initial heating. To keep water out of the interstitial particle void volume a water manager is often incorporated into exothermic compositions to absorb excess moisture. However, most water managers such as vermiculite and absorbent gelling material have particle sizes that are significantly larger than the iron particles due to the common practice in the art of using very fine iron particles based on the belief that the iron oxidation reaction is limited by the surface area of the iron particles. Thus, it has been conventionally believed that small iron particles increase the iron surface area. However, porosity is also an important factor in reaction rate. Thus, the size disparity between the particles of the water manager and iron can promote particle segregation and tight particle packing, thus inhibiting the reaction. For example, when the particle size ratio of the water manager to iron particles is greater than about 7:1, tight particle packing and inhibition of the reaction can occur.

Thus, with the present invention, exothermic compositions having a particular median particle size ratio of absorbent gelling material to iron powder are used to achieve the desired packing. The selected particle size distribution and ratio facilitates prevention of excess water in the interstitial particle void volume, and prevention of particle segregation and packing with void volumes such that faster rates of initial heating are achieved. The median particle size ratio of absorbent gelling material to iron powder in the present invention is from about 10:1 to about 1:10, alternatively from about 7:1 to about 1:7, alternatively from about 5:1 to about 1:5, and alternatively from about 3:1 to about 1:3.

Iron

It is believed that the exemplary particulate exothermic compositions defined herein release heat upon oxidation of the iron powder. There is no particular limit to the purity, kind, size, etc. of the iron powder as long as it can be used to produce heat generation via an oxidation reaction with water and air.

The particulate exothermic compositions of the present invention comprise one or more iron powder components at concentrations ranging from about 10% to about 90%, alternatively from about 30% to about 88%, and alternatively from about 50% to about 87%, by weight of the dry premix composition. Additionally, the system of the present invention can comprise greater than about 0.1 g iron powder/cm$^2$ of the water vapor generating portion.

Non-limiting examples of suitable sources for the iron powder include cast iron powder, reduced iron powder, electrolytic iron powder, scrap iron powder, sponge iron, pig iron, wrought iron, various steels, iron alloys, treated varieties of these iron sources, and combinations thereof.

Sponge iron is one source of the iron powder which may be particularly advantageous due to the high internal surface area of sponge iron. As the internal surface area is orders of magnitude greater than the external surface area, reactivity may not be controlled by particle size. Non-limiting examples of commercially available sponge iron include M-100 and F-417, which are available from the Hoeganaes Corporation located in New Jersey, USA.

Iron powder having a median particle size of from about 50 μm to about 400 μm, alternatively from about 100 μm to about 400 μm, and alternatively from about 150 μm to about 300 μm is suitable for use herein. Other sizes may likewise be suitable so long as the ratio of the median particle size of iron to the median size of absorbent gelling material is such that the size and distribution of particles provides for a particle packing with sufficient void volumes to allow substantially free access to air.

The median particle size of the iron powder, and any other particulate component defined herein, can be determined using a sieve method such as the method disclosed in ASTM Method B214. Generally, the particles are screened through a series of sieves consisting of different sizes, and the weight fraction of particles retained on each screen is measured. The weight fraction of the particles in each screen is then used to construct a cumulative weight distribution curve. The cumulative weight distribution curve is constructed by plotting particle size against the cumulatively added weight percent of particles less than the particle size retained on the next largest sieve. A median diameter is determined from the cumulative weight distribution curve, wherein the median diameter is defined as the particle size that corresponds with 50% of the cumulative weight. Details on constructing a cumulative weight distribution curve is described in "Methods of Presenting Size Analysis Data" in Particle Size Measurement, pages 153-156, 4th Edition, Terrence Allen, (1990).

Carbon

In exemplary particulate exothermic compositions according to one embodiment of the present invention comprise one or more carbon components at concentrations ranging from about 1% to about 25%, alternatively from about 1% to about 15%, and alternatively from about 1% to about 10%, by weight of the composition.

Non-limiting examples of carbon suitable for use herein include activated carbon, non-activated carbon, and mixtures thereof. The carbon component has a median particle size of from about 25 μm to about 200 μm, and alternatively from about 50 μm to about 100 μm. Activated carbon is particularly useful. In addition, combinations of the various carbons are also useful.

Activated carbon is extremely porous in the inner structure giving it particularly good oxygen adsorption capabilities. In fact, activated carbon has the ability to adsorb oxygen extremely well when the activated carbon is wetted, thus allowing for the activated carbon to function as a catalyst in the oxidation reaction. Thus, in the presence of a high water absorbing material such as for example absorbent gelling material or vermiculite, the availability of water to the carbon may be restricted and it may be important that activated carbon be pre-wetted prior to the addition of high water absorbing materials. Without being bound by theory, it is believed that activated carbon should be pre-wetted because of its inability to compete effectively against the high water absorbing material when the particulate pre-mix is dosed with brine. When activated carbon is pre-wetted, heat of adsorption is released such that the water adsorbed by the activated carbon is in a thermodynamically low energy state and thus the water does not migrate from the activated carbon to the high water absorbing material. Therefore, the activated carbon remains wet when the high water absorbing material is added, and is able to function as a catalyst for adsorbing oxygen.

In addition to its catalytic behavior, activated carbon has the capacity to absorb water, and can also serve as a water manager for the exothermic reaction. In addition, active carbon can adsorb odors such as those caused by the oxidation of iron powder.

Non-limiting examples of suitable carbons include activated carbon prepared from coconut shell, wood, charcoal, coal, bone coal, and the like, and combinations thereof are suitable for use herein, but those prepared from other raw materials such as animal products, natural gas, fats, oils, resins, and combinations thereof are also useful. There is no limitation to the kinds of activated carbon used. However, the preferred activated carbon has good oxygen adsorption capabilities. An example of a commercially available activated carbon includes activated carbon available from MeadWestvaco located in Covington, Va., USA.

Additionally, the amount of carbon in the particulate exothermic compositions defined herein should be minimal in order to maximize the interstitial particle void volume. Carbon is typically the finest particle component and excess carbon can result in the carbon filling up the interstitial particle void volume between the larger particles of the other materials. Thus, the amount of carbon needed for presenting an exothermic composition for generating moist heat is generally significantly lower than that used in conventional exothermic compositions because of the relatively high level of absorbent gelling material used herein. Therefore, the carbon herein is mainly used for its catalytic activity and minimally for its water retention property.

A low level of pre-wetted carbon is also highly desirable for high speed manufacture of the heat cells of the present invention because a low level of pre-wetted carbon enables the pre-mix to readily absorb the brine solution. With a high level of carbon, the brine absorption rate is slow due to wetting of the carbon. Thus, a low level of pre-wetted carbon significantly increases the rate of manufacture of the heat cells defined herein.

Absorbent Gelling Material

The particulate exothermic compositions of the present invention comprise one or more absorbent gelling materials at concentrations ranging from about 1% to about 25%, alternatively from about 1% to about 15%, and alternatively from about 1% to about 10%, by weight of the composition.

The absorbent gelling material ("AGM') suitable for use herein enables the retention of water physically or chemically within the particulate exothermic compositions of the present invention. In particular, the absorbent gelling material serves the function of storing water for release to the iron powder component and releasing the water in a controlled manner. Upon heating, stored water is released form the AGM and is converted to water vapor by absorbing heat, thus storing heat energy as latent heat of vaporization in the water vapor. Additionally, a portion of the stored water may be utilized to maintain the activated carbon moisture level. By storing excess water in the AGM instead of the interstitial particle void volume, the exothermic composition in the heat cell is able to rapidly oxidize the iron and generate an internal temperature high enough to produce water vapor generated from the water stored in the AGM. Because of the AGM's high water holding capacity, the exothermic composition in the heat cells remains highly reactive over a sustained period of time. While not wishing to be bound by any theory, it is believed that the AGM may prevent or inhibit liquid water from entering and/or being maintained in the interstitial voids of particulate exothermic compounds thereby facilitating prevention of flooding of the exothermic composition.

Non-limiting examples of suitable absorbent gelling materials include those absorbent gelling materials that have fluid-absorbing properties and can form hydrogels upon contact with water. An example of such an absorbent gelling material is the hydrogel-forming, absorbent gelling material that is based on a polyacid, for example polyacrylic acid. Hydrogel-forming polymeric materials of this type are those which, upon contact with liquids such as water, imbibe such fluids and thereby form the hydrogel. These particularly useful absorbent gelling materials generally comprise substantially water-insoluble, slightly cross-linked, partially neutralized, hydrogel-forming polymer materials prepared from polymerizable, unsaturated, acid-containing monomers. In such materials, the polymeric component formed from unsaturated, acid-containing monomers can comprise the entire gelling agent or can be grafted onto other types of polymer moieties such as starch or cellulose. Acrylic acid grafted starch materials are of this latter type. Thus, specific suitable absorbent gelling materials include hydrolyzed acrylonitrile grafted starch, acrylic acid grafted starch, polyacrylate, maleic anhydride-based copolymer, and combinations thereof. The polyacrylates and acrylic acid grafted starch materials are particularly useful. Non-limiting examples of commercially available polyacrylates include those polyacrylates which are available from Nippon Shokubai located in Chatanooga, Tenn., USA.

The absorbent gelling material has a median particle size of from about 300 µm to about 800 µm, alternatively from about 400 µm to about 800 µm, and alternatively from about 500 µm to about 800 µm. Absorbent gelling materials having a median particle size of 300 µm or greater have been shown to contribute to minimal or no particle segregation effects. Reducing segregation effects provides for improved sustained temperature such that the desired heat benefits are achieved without adverse events such as skin burns. Reducing segregation effects also allows for the high-speed production of portable moist heat delivery devices comprising a plurality of heat cells and that provide for up to four or five hours of moist heat.

As described above, the particulate exothermic compositions defined herein have particular median particle size ratios of absorbent gelling material to iron powder. It has been found that exothermic compositions comprising the defined select median particle size ratios of these components exhibit minimal or no segregation effects which result in exothermic compositions that meet the intended thermal behavior for the desired moist heat benefits.

In addition to the absorbent gelling material, the particulate exothermic compositions of the present invention can optionally comprise other water-holding materials that have capillary function and/or hydrophilic properties. These optional water-holding materials can be included in the particulate exothermic compositions at concentrations ranging from about 0.1% to about 25%, alternatively from about 0.5% to about 20%, and alternatively from about 1% to about 15%, by weight of the composition. Non-limiting examples of such optional water-holding materials include vermiculite, porous silicates, wood powder, wood flour, cotton, paper, vegetable matter, carboxymethylcellulose salts, inorganic salts, and combinations thereof. Absorbent gelling material and optional water-holding materials are further described in U.S. Pat. Nos. 5,918,590 and 5,984,995.

Metal Salt

The particulate exothermic composition of the present invention comprises one or more metal salts at concentrations ranging from about 0.5% to about 10%, alternatively from about 0.5% to about 7%, and alternatively from about 1% to about 5%, by weight of the composition.

Non-limiting examples of metal salts suitable for use herein include those metal salts that serve as a reaction promoter for activating the surface of the iron powder to ease the oxidation reaction with air and provide electrical conduction to the exothermic composition to sustain the corrosive (i.e., oxidative) reaction. In general, several suitable alkali, alkaline earth, and transition metal salts exist which can be used, alone or in combination, to sustain the corrosive reaction of iron.

Non-limiting examples of suitable metal salts include sulfates, chlorides, carbonate salts, acetate salts, nitrates, nitrites, and combinations thereof. Specific non-limiting examples of sulfates include ferric sulfate, potassium sulfate, sodium sulfate, manganese sulfate, magnesium sulfate, and combinations thereof. Specific non-limiting examples of chlorides include cupric chloride, potassium chloride, sodium chloride, calcium chloride, manganese chloride, magnesium chloride cuprous chloride, and combinations thereof. Cupric chloride, sodium chloride, and mixtures thereof are particularly useful metal salts. An example of a commercially available sodium chloride includes the sodium chloride available from Morton Salt located in Chicago, Ill. (USA).

Water

The particulate exothermic compositions of the present invention comprise water at concentrations ranging from about 1% to about 50%, alternatively from about 1% to about 35%, and alternatively from about 5% to about 33%, by weight of the composition. Water suitable for use herein can be from any appropriate source, non-limiting examples of which include tap water, distilled water, deionized water, or any mixture thereof.

It is known that the thermal performance of exothermic heat cells is highly sensitive to moisture level, with small amounts of water providing only short time of reaction and too much water slowing the desired heating rate and/or flooding the heat cell and terminating the reaction In a device that generates moist heat, one challenge is that a supply of water is needed to create the water vapor for the moist heat. It has been found, however, that the particulate exothermic compositions with interstitial spaces formed by selection of size and distribution of particle sizes of iron and AGM of the present invention not only provide heat cells that are highly effective in generating high amounts of water vapor exceeding 0.25 grams of water vapor per cell over the course of the reaction, but also provide heat cells that have fast initial heating times to achieve desired temperatures quickly. This is achieved by incorporating a sufficient weight ratio of water to absorbent gelling material such that the particulate exothermic compositions have high internal water retention (preferably with the AGM acting as the principal repository) and high interstitial particle void volumes. The particulate exothermic compositions of the present invention comprise a weight ratio of water to absorbent gelling material of from about 3:1 to about 9:1, and alternatively from about 4:1 to about 7:1, by weight of the exothermic composition.

The particulate exothermic compositions of the present invention can comprise a high level of water and yet be constructed at lower cell weight levels than current heat cells. Therefore, the exothermic compositions of the present invention are utilized more effectively with high water concentration, and less exothermic composition is needed to achieve the desired amount and duration of water vapor generation.

Optional Components

The exothermic compositions of the present invention can further comprise one or more optional components known or otherwise effective for use in exothermic compositions, provided that the optional components are physically and chemically compatible with the compositional components described hereinabove, or do not otherwise unduly impair product stability, aesthetics, or performance.

Optional components suitable for use herein include materials such as agglomeration aids for agglomeration of particles, non-limiting examples of which include corn syrup, maltitol syrup, crystallizing sorbitol syrup, and amorphous sorbitol syrup; dry binders, non-limiting examples of which include microcrystalline cellulose, microfine cellulose, maltodextrin, sprayed lactose, co-crystallized sucrose and dextrin, modified dextrose, mannitol, pre-gelatinized starch, dicalcium phosphate, and calcium carbonate; oxidation reaction enhancers non-limiting examples of which include elemental chromium, manganese, copper, and compounds comprising said elements; hydrogen gas inhibitors, non-limiting examples of which include inorganic and organic alkali compounds, and alkali weak acid salts, specific non-limiting examples of which include sodium thiosulfate, sodium sulfite, sodium hydroxide, potassium hydroxide, sodium hydrogen carbonate, sodium carbonate, calcium hydroxide, calcium carbonate, and sodium propionate; fillers non-limiting examples of which include natural cellulosic fragments including wood dust, cotton linter, and cellulose, synthetic fibers in fragmentary form including polyester fibers, foamed synthetic resins such as foamed polystyrene and polyurethane, inorganic compounds including silica powder, porous silica gel, sodium sulfate, barium sulfate, iron oxides, and alumina; anti-caking agents non-limiting examples of which include tricalcium phosphate and sodium silicoaluminate; and mixtures thereof.

Such components also include thickeners, non-limiting examples of which include cornstarch, potato starch, carboxymethylcellulose, and alpha-starch; and surfactants non-limiting examples of which include anionic, cationic, non-ionic, zwitterionic, and amphoteric surfactants. Still other optional components can be included within the compositions or systems herein, as appropriate, including extending agents, non-limiting examples of which include metasilicates, zirconium, and ceramics, and mixtures thereof. The optional components can be included in the particulate exothermic compositions at concentrations ranging from about 0.01% to about 35%, and alternatively from about 0.1% to about 30%, by weight of the composition.

Oxygen is necessary for the oxidation reaction to occur. However, in the exemplary embodiments presented herein an internal oxygen source is not required. Optionally, in other embodiments within the scope of the moist heat delivery systems, an oxygen-producing chemical material may be incorporated in the particulate exothermic composition at the time of preparation thereof. Non-limiting examples of oxygen sources suitable for use with the present invention include air and artificially made oxygen of various purity. Air is particularly useful because it is convenient and inexpensive.

Heat Cells

The heat cells of the water vapor generating portion of the present invention can comprise particulate exothermic compositions that utilize an exothermic iron oxidation reaction system to provide a water vapor source. A heat cell comprised of a particulate exothermic composition and used as a water vapor source to deliver moist heat should have a particulate exothermic composition capable of remaining highly reactive even with high water content. High water content provides high rate of water vapor generation for an extended period of time. The particulate exothermic composition provides rapid water vapor generation at temperatures safe for contact with human skin when the heat cells are incorporated into a water vapor generating portion of portable moist heat delivery systems. The water vapor generation portion is in communication with the water vapor-air regulation portion, which adjusts the dew point of the water vapor to a pre-selected temperature (i.e., one that will not burn skin) by regulating the proportion of water vapor and air in the water vapor-air mixture.

The exothermic compositions of the present invention are particulate exothermic compositions. As used herein "particulate" refers to separate particles contained within the compositions. The particulate exothermic compositions defined herein contain separate particles wherein each particle has a median particle size ranging from about 25 µm to about 800 µm. In certain embodiments, a range of particles sizes may be preferred to yield a composition with desired interstitial pore space.

In an exemplary embodiment, an exothermic composition is prepared by preparing a premix of wetted carbon, iron, and AGM, which is subsequently treated with a brine solution. According to one embodiment, the compositions may comprise from about 10% to about 90% by weight of iron powder; from about 1% to about 25% by weight of a carbon selected from activated, non-activated carbon and mixtures thereof; from about 1% to about 25% or alternatively about 2% to about 12% by weight of an AGM; and from about 1% to about 50%, alternatively from about 1% to about 35%, or from about 15% to about 35% by weight of water. One exemplary single heat cell of the present invention can comprise from about 0.4 g of pre-mix per cell to about 2.5 g of pre-mix per cell, and from about 0.4 g of brine solution per cell to about 1.5 g of brine solution per cell. A heat cell of the present invention can comprise a total cell weight, per cell, of from about 0.8 g to about 10.0 g, alternatively from about 1.5 g to about 3.5 g, and alternatively from about 2.5 g, to about 3.0 g. In certain embodiments of the moist heat delivery system, a plurality of heat cells may be used in the system.

As described above, selection of the particle size of the particulate components, e.g., the iron and AGM, of exothermic compositions may be important for minimization of particle separation or segregation within an exothermic composition. Particle size directly effects particle mobility and particulate components can vary in their mobility resulting in particle separation or segregation. The exothermic compositions defined herein preferably comprise particulate components having defined median particle size ranges such that the exothermic compositions resist particle separation or segregation. It is contemplated, however that particulate components having median particle sizes ranges above or below the ranges defined herein are suitable for use in the exothermic compositions defined herein.

The heat cells of the present invention are small compared to most conventional commercial heat cells, and excess levels of exothermic composition cannot be used to compensate for particle segregation effects. As described above, particle segregation effects are reduced in the particulate exothermic composition of the present invention by using iron powder in a particular ratio with absorbent gelling material. Without being bound by theory, it is believed that the oxidative reaction rate of such exothermic compositions is controlled by the porosity of the exothermic composition. The accessibility of oxygen through the particulate exothermic composition is affected by the packing behavior of the particles, i.e. the interstitial void volume, and by the amount of water present in the exothermic composition.

In one exemplary embodiment, the heat cell is formed in a unified structure comprising at least two opposed surfaces, preferably, one substantially non-air-permeable and non-moisture-permeable surface, such as a film layer substrate material and one aerated skin-facing surface that is highly air-permeable and moisture-permeable, such as a polymer non-woven material. To direct moist heat toward the skin, the air and moisture permeable side of the heat cell is disposed toward the latent heat delivery surface and skin-facing side of the moist heat delivery system. In one embodiment, the air and moisture permeable surface may be interposed between the heat cell and the water vapor-air regulating portion of the moist heat delivery system and the water vapor-air regulating portion may be interposed between the heat cell and the latent heat transfer surface/hair facing surface. The substantially non-air-permeable surface may either be the external surface or oriented proximate the external surface.

Uniform heating and water vapor generation may be provided by using a plurality of heat cells. By using a plurality of heat cells, the size of an individual heat cell can be reduced. The relatively small size of the heat cells, and their spacing in the system of the present invention enable even air flow to the heat cells. In addition, the water vapor generated can be controlled by the number of heat cells used, and their spacing. By way of non-limiting example, in one embodiment two portable moist heat delivery systems of the same size and composition (i.e., the same in all respects except number of heat cells and the spacing between the heat cells), a system made with 24 heat cells has a water vapor generation rate that is less than two times the water vapor generation rate of a system made with 12 heat cells, yet lasts four times as long. Without being bound by theory, the non-linear water vapor generation and duration relationship is believed to be due to the fixed surface area of the system that is accessible to air. Thus, reaction rate, water vapor generation rate and duration of heat generation can be controlled by the number of heat cells used and their spacing.

The Aerated Skin-Facing Surface of the Heat Cell

The aerated skin-facing surface of the heat cells (e.g., "aerated heat cell surface") can serve a dual function providing air to the particulate exothermic composition in the water vapor generating portion and preventing the particulate exothermic composition from leaking out of the heat cell, as well as forming a water vapor-air mixing layer as part of the water vapor-air regulating portion. The aerated skin-facing surface impacts regulation of mixing of water vapor and air, particularly when the system is used in a vertical orientation. Variation of the aerated skin-facing surface can thus be used to regulate the amount of air mixed with the generated water vapor to help lower the dew point temperature of the water vapor-air mixture. However, because of its high air permeability the aerated skin-facing surface has no limiting effect on the reaction rate, and particularly the water vapor generation rate, of the system.

The aerated surface of the heat cell facing the skin can be formed of an SMMS (spunbond-meltblown-meltblown-spunbond) material, a SMS (spunbond-meltblown-spunbond) material, a spun-bond material, a melt-blown material, mesh, woven fabric and combinations thereof that can vary in basis weight from about 15 gsm (grams per square meter) to about 90 gsm, and alternatively from about 15 gsm to about 76 gsm. In an SMMS material, the "S" layers in the structure provide strength and air entry, while the two "M" layers are made of much finer denier filaments that function to prevent the smaller carbon particles from leaking out of the cells. Non-limiting examples of suitable materials used for an SMMS layer include polypropylene, polyethylene, polyester or other suitable polymer materials known to those skilled in the art.

The aerated surface of the heat cell facing the skin can have an air-permeability of greater than about 25 $cm^3/cm^2/sec$ and can have a moisture vapor transmission rate greater than about 5,000 $g/m^2/24$ hr. The aerated surface can have a thickness of from about 0.05 mm to about 1 mm, alternatively from about 0.1 mm to about 0.8 mm, and alternatively of about 0.4 mm The Opposed Surface of the Heat Cell The opposed, non-air- or semi-air-permeable/non-moisture- or semi-moisture-permeable surface of the heat cell can be made of films or films laminated to non-woven fabrics to form a film layer substrate. In general, suitable films are those having heat sealability and are capable of being easily thermally fused. Non-woven materials, if used, provide support and integrity to the film layer substrates. Non-limiting examples of suitable films include polyethylene, polypropylene, nylon, polyester, polyvinyl chloride, vinylidene chloride, polyvinylidene chloride, polyurethane, polystyrene, saponified ethylene-vinyl acetate copolymer, ethylene-vinyl acetate copolymer, natural rubber, reclaimed rubber, and synthetic rubber, and combinations thereof. The film layer substrate has a thickness in the range of about 1 μm to about 300 μm and may be non-air- or semi-air-permeable and non-moisture- or semi-moisture-permeable. For non-woven fabric, if used, those having preferred characteristic properties of light weight and high tensile strength, e.g., nylon, rayon, cellulose ester, polyvinyl derivatives, polyolefins, polyamides, or polyesters, are suitable.

A non-limiting example of a preferred non-woven material is a SMMS laminated structure of from about 15 gsm to about 100 gsm (grams per square meter) basis weight, in specific embodiments with a meltblown layer of basis weight of from about 2 gsm to about 16 gsm, alternatively from about 4 gsm to about 10 gsm and alternatively from about 6 gsm to about 8 gsm. Such non-woven materials are generally described in Riedel "Nonwoven Bonding Methods and Materials", Nonwoven World, (1987). An example of a commercially available non-woven sheet is material number W502FWH, which is commercially available from PGI (Polymer Group International) located in Waynesboro, Va., USA or FQN (First Quality Nonwoven) located in Haxle Township, Pa., USA.

Non-limiting examples of useful film layer substrates include polypropylene non-woven sheets laminated to a film of poly(ethylene-vinyl acetate) or low-density polyethylene (LDPE) having a thickness of from about 5 μm to about 100 μm. An example of a commercially available polypropylene/ethylene vinyl acetate (PP/EVA) film is material number DH245, which is commercially available from Clopay Plastics of Cincinnati, Ohio U.S.A.

The heat cell may be formed by bonding the opposed surfaces of the aerated surface material and the non/semi-permeable film together around their periphery thereby forming a pouch, envelope, or pocket. Pockets can also be made in the non/semi-air and non/semi-moisture permeable substrate by vacuum, thermoforming, mechanical embossing, vacuum embossing, or other acceptable means. Preferred for use herein is thermoforming which is described in "Thermoforming", The Wiley Encyclopedia of Packaging Technology, pp. 668-675 (1986), Marilyn Bakker, ed.

When filled with a particulate exothermic composition, each heat cell has a fill volume, void volume, and a cell volume. The fill volume, as used herein, means the volume of the particulate composition in the filled heat cell. The void volume, as used herein, means the volume of the cell left unfilled by the particulate composition in a finished heat cell, measured without differential pressure in the heat cell and without additional stretching or deformation of the substrate materials. The cell volume, as used herein, means the fill volume plus the void volume of the heat cell. The ratio of fill volume to cell volume is from about 0.7 to about 1.0, alternatively from about 0.75 to about 1.0, more alternatively from about 0.8 to about 1.0, alternatively from about 0.85 to about 1.0, and alternatively from about 0.9 to about 1.0.

A heat cell can also be measured in terms of its height or thickness of the heat cell at the point of greatest thickness. In an exemplary embodiment, the thickness of a heat cell at the point of greatest thickness may be from greater than about 0.2 cm (centimeters) to about 1.0 cm, preferably from greater than about 0.3 cm to about 0.9 cm, alternatively from about 0.4 cm to about 0.8 cm, and alternatively from about 0.5 cm to about 0.7 cm.

The resulting heat cell can have any geometric shape, e.g., disk, triangle, pyramid, cone, sphere, square, cube, rectangle, rectangular parallelepiped, cylinder, ellipsoid and the like. The shape of the heat cell can be elongated in its geometry, with the long axis parallel to the substrates, having a height of from about 0.2 cm to about 5 cm, alternatively from greater than about 0.5 cm to about 1 cm, a width of from about 0.2 cm to about 20 cm, alternatively from about 5 cm to about 10 cm, and a length of from about 1 cm to about 20 cm, alternatively from about 5 cm to about 10 cm, resulting in a cell volume of from about 0.04 $cm^3$ to about 2,000 $cm^3$, or 0.04 $cm^3$ to about 30 $cm^3$ and alternatively from about 1.25 $cm^3$ to about 10 $cm^3$.

Alternatively the shape can be a disk shaped geometry having a cell diameter of from about 0.2 cm to about 5 cm, of from about 1 cm to about 4 cm, alternatively from about 2 cm to about 3 cm, and a height of from about 0.2 cm to about 1 cm, alternatively from about 0.3 cm to about 0.9 cm, alternatively from about 0.4 cm to about 0.8 cm, and alternatively from about 0.5 cm to about 0.7 cm, resulting in a cell volume of from about 0.0045 $cm^3$ to about 20 $cm^3$, alternatively from about 0.2 $cm^3$ to about 1 $cm^3$.

The heat cell can have a planar view surface area, per cell, of from about 0.03 $cm^2$ about 20 $cm^2$, alternatively from about 0.1 $cm^2$ to about 20 $cm^2$, and alternatively from about 1 $cm^2$ to about 20 $cm^2$. Heat cells with this area per cell are easily incorporated into flexible devices which provide improved conformity with body forms; provide even, uniform heat to a target area; and improve wearer comfort.

The heat cell can have a pre-mix weight of from about 0.4 g of pre-mix per cell to about 2.5 g of pre-mix per cell, alternatively from about 1.0 g of pre-mix per cell to about 2.4 g of pre-mix per cell, and alternatively from about 1.5 g of pre-mix per cell to about 2.3 g of pre-mix per cell. Heat cells with this weight of pre-mix per cell are also easily incorporated into flexible devices and systems which provide improved conformity with body forms; provide even, uniform heat to a target area; and improve wearer comfort.

In one exemplary embodiment of the moist heat system, a plurality of heat cells are used. All of the heat cells may be moist heat generators or a component of a moist heat generator, or alternatively a portion of the heat cells may be moist heat generators or component of moist heat generators used in combination with dry heat cells.

According to an exemplary moist heat wrap comprising one or more moist heat delivery systems in which the water vapor source is incorporated into heat cells, the water vapor source may comprise a planar area from about 25% to about 90%, alternatively from about 25% to about 75%, and alternatively from about 25% to about 60% of the total planar area of the water vapor generating portion.

Water Vapor-Air Regulating Portion

The moist heat delivery system of the present invention contains a water vapor generating portion as described above. The water vapor generating portion preferably selectively directs water vapor toward the water vapor-air regulating portion. As described herein, in one exemplary embodiment this may be accomplished using a permeable film on one side of the water vapor generating device and an impermeable film on the other side of the water vapor generating devise. The water vapor-air regulator portion provides for adjustment of dew point temperature. The water vapor generating portion is in fluid communication with the water vapor-air regulating portion and reduces the dew point temperature of the water vapor-air mixture exiting the system to a safe temperature for delivery of latent heat to the hair of the user. Optionally, the water vapor-air regulating portion may orient water vapor generated by the water vapor generation portion towards the latent heat delivery surface and ultimately a user's body or skin to provide a comfortable device that can he held against the skin, held near the skin with a controlled and pre-selected amount of gap between the surface and the skin, adhesively adhered to the skin, or placed in a holder, such as, for example, a reusable fabric pocket, a wrap, or a contoured device that is held in place at least partially by conforming to a body surface, such as the head, and that holds the water vapor generation portion and/or water vapor-air regulating portion in place against the desired body part. In one exemplary embodiment, the water vapor-air regulating portion or, alternatively, a portion of the water vapor-air regulating portion may be included in the structure of the holder. The holder may be a single use, disposable holder or a multi use, reusable holder. The holder may be held in place by any of a variety of means known in the art including, but not limited to, adhesives, fasteners, ties, interlocking parts, buttons, snaps, or combinations thereof.

According to one exemplary embodiment, the water vapor-air regulating portion can comprise at least one water vapor-air mixing layer and at least one water vapor-air distribution layer. The layers are arranged such that water vapor and air can pass among and between the layers and the water vapor generating portion. The water vapor-air regulating portion can facilitate an even flow of air into, and water vapor out of, the water vapor generating portion, particularly when the system is used in a manner that compresses the system. To minimize the effect of compression, it may be desirable to use a water vapor mixing layer that is resistant to compression. One example of such a material is a needle punched nonwoven material. The water vapor-air regulating portion can also comprise one or more latent heat transfer surfaces and/or skin contact layers. The latent heat transfer surface/skin contact layer may be a surface of a portion of the water vapor-air regulating portion or, alternatively, a layer or layers of material.

According to one embodiment, the air permeability of the water vapor-air regulating portion comprising the water vapor-air mixing layer, the water vapor-air distribution layer and latent heat delivery surface and optional skin contact layer is from about 25 cm$^3$/cm$^2$/sec to about 8000 cm$^3$/cm$^2$/sec, alternatively from about 300 cm$^3$/cm$^2$/sec to about 8000 cm$^3$/cm$^2$/sec, and alternatively from about 500 cm$^3$/cm$^2$/sec to about 7000 cm$^3$/cm$^2$/sec, measured using ASTM Method No. D737. According to another embodiment, the air permeability of the water vapor-air regulating portion comprising the water vapor-air mixing layer, the water vapor-air distribution layer and latent heat delivery surface and optional hair contact layer is from about 25 cm$^3$/cm$^2$/sec to about 100 cm$^3$/cm$^2$/sec, alternatively from about 30 cm$^3$/cm$^2$/sec to about 70 cm$^3$/cm$^2$/sec, alternatively from about 40 cm$^3$/cm$^2$/sec to about 60 cm$^3$/cm$^2$/sec, and alternatively about 50 cm$^3$/cm$^2$/sec, measured using ASTM Method No. D737. Appropriate air permeability may depend, for example on the use of the moist heat delivery system, such as for delivery of skin care actives. The moisture vapor transmission rate of the water vapor-air regulating portion is from about 500 g/m$^2$/24 hr to about 2,500 g/m$^2$/24 hr, alternatively from about 1,000 g/m$^2$/24 hr to about 2,000 g/m$^2$/24 hr, and particularly greater than about 1400 g/m$^2$/24 hr, as measured using ASTM Method No. E96. In one exemplary embodiment, the water vapor-air regulating portion may comprise one or more water vapor-air mixing layers and one or more water vapor-air distribution layers.

In one exemplary embodiment, a particularly useful arrangement is to use a single water vapor air distribution layer and a single water vapor-air mixing layer. In this embodiment the moist heat system is incorporated into a moist heat wrap and/or pack. It is critical that the perimeter of the moist heat wrap or pack is heat sealed so that the perimeter of the single water vapor air distribution layer and the single water vapor-air mixing layer of the moist heat system are sealed within the perimeter of the moist heat wrap pack. In a preferred embodiment, the water-vapor air distribution layer may be constructed of a foam material in which the base material of the foam is substantially impermeable to air and water vapor but which has channels and/or apertures which allow passage of air and/or water vapor. The water vapor air distribution layer comprising a perforated foam layer heat sealed around the perimeter restricts air from coming into the perimeter of the moist heat wrap. As a result, the size and number apertures and/or channels in the water vapor distribution layer acts to regulate the system by allowing sufficient air for generating the water vapor while also allowing the exiting water vapor to easily move out of the wrap toward the skin, thus regulating the reaction rate and in turn the amount of water vapor generated. By regulating the amount of water vapor generated, the water vapor regulating portion of the device can be simplified. Moreover, for embodiments using thermal cells, regulation of the amount of air for reaction may also facilitate the control of the heating of the heat cells so that the cells do not reach an excessively high temperature. In one exemplary embodiment, a single layer of 0.8 mm (1/32 inch) foam may be sufficient to allow for both good moist heat production and transfer performance and for safe handling of a replaceable moist heat pack with the hands for removal of the pack from air tight packaging, which initiates activation, and installation into a reusable heat wrap or holder. A thin moist heat pack that is convenient to handle is desirable for use in a semi-durable moist heat wrap or other semi-durable moist heat device, since it allows for safe handling of the disposable moist heat pack and convenient reuse of at least a portion of the wrap.

In certain embodiments, for constructing the water vapor-air regulating portion, one or more water vapor-air mixing layers may be used, one or more water vapor-air distribution layers can be used, and one or more skin contact layers may be used. In one exemplary embodiment, a particularly useful arrangement is to use two water vapor-air mixing layers and two water vapor-air distribution layers, alternating between the two, with the first water vapor-air mixing layer adjacent the water vapor generating portion. Alternatively a water vapor-air distribution layer can be placed adjacent the water vapor generating portion. Alternatively, as described above, a water vapor air mixing layer can also be physically formed in integral association with the water vapor generating portion.

The system of the present invention is designed to allow an exothermic water vapor source to operate at a high temperature, from about 50° C. to about 70° C., to maximize water vapor production delivering latent heat and moisture to the user at a pre-selected temperature that does not harm/burn the skin. As water vapor and the condensation of water vapor to release latent heat are important to the energy transfer in a moist heat system, the pre-selected temperature for the moist heat system in a preferred embodiment is the dew point temperature of the water vapor-air mixture proximate the latent heat transfer surface and/or skin contact layer. Thus, the system provides both protection from thermal damage to the user and maintains an ideal water vapor generating environment that stores and subsequently releases heat energy at the desired location.

The inventors have surprisingly discovered that dew point temperatures higher than about 43° C. may be used in certain instances without harming the skin. Without being held to any theory, it is believed that this is because sufficient latent heat energy delivered to the skin may stimulate circulation and facilitate dissipation of the heat energy to avoid harm. Alternatively, the design of the device may modify the contact time of the water vapor with the skin such that the contact time is insufficient to condense all of the water vapor; hence reducing the energy transfer to the skin.

In one embodiment, the water vapor is made safe for skin contact by regulating the mixture of water vapor and air to a water vapor to dry air ratio of less than about 0.065 kg water/ kg dry air. By regulating the ratio of water vapor to air, the water vapor in the water vapor-air mixture will condense at a dew point temperature such that heat can be optimally and safely transferred to a user's skin without the risk of thermal injury. As used herein, "dry air" refers to air with no appreciable water content.

Although the descriptions herein include one exemplary embodiment using two pairs of water vapor-air mixing layers and two pairs of water vapor-air distribution layers, one skilled in the art will appreciate that the same effects could be achieved with one, two, or more water vapor-air mixing layers and/or one, two, or more water vapor-air distribution layers, or some combination thereof may also be used in the device. Adjustment of the location, thickness, air permeability, and moisture vapor transmission rate of each layer and/or type of material may be desirable to create a suitable thermal and air mixing environment, for example in those embodiments having a plurality of mixing layers and/or distribution layers.

In one exemplary embodiment, the ratio of water vapor to dry air can be regulated by utilizing one or more longitudinal strips, as described below, disposed parallel to a row of multiple heat cells. In one embodiment, one water vapor-air mixing layer can be used in combination with longitudinal strips of foam positioned at the skin-facing side of the water vapor-air mixing layer. The strip(s) may function as a portion of the water vapor-air regulating portion. The longitudinal strips can serve to create an air space parallel to a row of multiple heat cells. The air space can aid in providing even flow of air into the water vapor generating portion, and aid in water vapor-air mixing. The height of the longitudinal strips can be adjusted such that the ratio of water vapor to dry air is less than 0.065 kg water/kg of dry air, and alternatively less than about 0.060 kg water/kg dry air. Without wishing to be held to any theory, it is believed that one or more strip over a plurality of heat cells may enable the plurality of heat cells covered by the strip(s) to act and/or be impacted cooperatively. In specific embodiments, it may not be necessary that all heat cells be grouped and/or aligned in rows and covered by a strip. In certain embodiments, only one row or group or a portion of the rows or groupings of heat cells may be covered with a strip.

Water Vapor-Air Mixing Layer

In one exemplary embodiment, at least one water vapor-air mixing layer can comprise an aerated structure of between about 18 gsm to about 430 gsm (grams per square meter), or from about 50 gsm to a bout 150 gsm, or even about 50 gsm and about 100 gsm, and alternatively about 70 gsm to about 90 gsm. The at least one water vapor-air mixing layer can have a caliper-measured thickness according to ASTM Method No. D5729 of from about 1 mm to about 19 mm, alternatively from about 1 mm to about 5 mm, alternatively from about 0.1 mm to about 4 mm or from about 1 mm to about 4 mm, and particularly of about 3 mm. Non-limiting examples of materials suitable for the water vapor-air mixing layer include woven materials; non-woven materials including wet-laid, air-laid, point-bonded, needle-punched and thermally bonded non-woven materials; fabrics; polyethylene; polypropylene; polyester; wood pulp; rayon; fibrous plant-based materials including celluloses, wool, silk, jute, hemp, cotton, linen, sisal, ramie; and combinations thereof.

The at least one water vapor-air mixing layer has an air permeability of from about 400 $cm^3/cm^2$/sec to about 17,000 $cm^3/cm^2$/sec, or even from about 500 $cm^3/cm^2$/sec to about 2,000 $cm^3/cm^2$/sec, and alternatively from about 1,000 $cm^3/cm^2$/sec to about 1,500 $cm^3/cm^2$/sec, as measured by ASTM Method No. D737, and a moisture vapor transmission rate of from about 5,000 $g/m^2$/24 hr to about 7,000 $g/m^2$/24 hr, and alternatively from about 5,500 $g/m^2$/24 hr to about 6,500 $g/m^2$/24 hr, as measured by ASTM Method E96.

Water Vapor-Air Distribution Layer

In one exemplary embodiment, at least one water vapor-air distribution layer can comprise a layer of insulative material having a caliper-measured thickness, according to ASTM Method No. D5729, of from about 0.1 mm to about 13 mm, alternatively from about 0.5 mm to about 6 mm, and alternatively from about 1 mm to about 2 mm. In another embodiment, the layer of insulative material may have a caliper-measured thickness of from about 0.1 mm to about 3 mm, alternatively from about 0.5 mm to about 2 mm, and particularly about 1 mm. In one embodiment, the at least one water vapor-air distribution layer can have a basis weight of from about 5 gsm to about 430 gsm, alternatively from about 5 gsm to about 50 gsm, and alternatively from about 5 gsm to about 25 gsm, as measured by ASTM Method No. D3776. In another embodiment, the at least one water vapor-air distribution layer can have a basis weight of from about 5 gsm to about 30 gsm, alternatively from about 7 gsm to about 12 gsm, and particularly about 10 gsm, as measured by ASTM Method No. D3776. The material of the water vapor-air distribution layer is substantially air and moisture impermeable, and can be resistant to compression.

Non-limiting examples of materials suitable for the water vapor-air distribution layer include polyethylene-based foam, polypropylene-based foam, polyester-based foam, polystyrene-based foam, polyurethane-based foam, foamed plastic sheet, plastic film, foil, paper-foil laminate, paper, non-woven, sponge, glass wool, fiberglass, and combinations thereof.

The air and moisture impermeable material can have an air permeability of less than about 0.025 $cm^3/cm^2$/sec, measured using ASTM Method No. D737, and a moisture vapor transmission rate of less than about 200 $g/m^2$/24 hr as measured using ASTM Method No. E96. In one embodiment, the material can also have a thermal conductivity of from about 0.5 W/m*K to about 285 W/m*K (K=degrees Kelvin) and a density of from about 5 $kg/m^3$ to about 150 $kg/m^3$. In another embodiment, the material can also have a thermal conductivity of from about 0.25 W/m*K to about 0.5 W/m*K (K=degrees Kelvin) and a density of from about 5 $kg/m^3$ to about 15 $kg/m^3$. Thermal conductivity of this material can be obtained from the following source: "For Computer Heat-Conduction Properties data" A.L. Edwards, UCRL-505 Copyright K&K Associates 1997.

In certain embodiments, it may be desirable to selectively perforate the air and moisture impermeable material to form the water vapor-air distribution layer and allow passage of air and water vapor through to the user, and to allow air to enter and to reach the water vapor generating portion, particularly if an exothermic oxidation reaction is used as the mechanism for water vapor generation. Alternatively, apertures and/or channels may be employed to allow passage of air and water vapor-air mixtures.

While the materials used for the water vapor-air distribution layer may be substantially impermeable to air and water vapor, they should be assembled, constructed or configured such that the overall air permeability of the vapor-air distribution layer is for one embodiments from about 500 $cm^3/cm^2$/sec to about 2500 $cm^3/cm^2$/sec, alternatively about 1000 $cm^3/cm^2$/sec to about 2500 $cm^3/cm^2$/sec, and alternatively about 1500 $cm^3/cm^2$/sec to about 2300 $cm^3/cm^2$/sec as measured by ASTM Method D737. In another embodiment, the overall air permeability may range from about 100 $cm^3/cm^2$/sec to about 300 $cm^3/cm^2$/sec, alternatively greater than about 150 $cm^3$/ cm²/sec and alternatively greater than about 200 cm³/cm²/sec as measured by ASTM Method D737. The moisture vapor transmission rate of the vapor-air distribution layer is from about 6,000 g/m²/24 hr to about 9,000 g/m²/24 hr, alternatively from about 7,000 g/m²/24 hr to about 8,500 g/m²/24 hr, alternatively from about 7,500 g/m²/24 hr to about 8,500 g/m²/24 hr, and preferably about 8,100 g/m²/24 hr as measured by ASTM Method E96.

Longitudinal Strips

As described herein, in certain embodiments, the water vapor-air regulating portion can also comprise longitudinal strips. Longitudinal strips can be used to provide additional air to the system for reaction and to provide additional water vapor-air mixing. The longitudinal strips can comprise any flexible and non-compressible material. The height of the longitudinal strips can be adjusted to achieve a desired water vapor to air ratio of less than about 0.085 kg water/kg dry air, or even less than about 0.065 kg water/kg dry air, and alternatively less than about 0.060 kg water/kg dry air. Non-limiting examples of materials suitable for use in the longitudinal strips include polyethylene-based foam, polypropylene-based foam, polystyrene-based foam, polyurethane-based foam, foamed plastic sheet, plastic film, foil, paper-foil laminate, non-wovens, sponge, glass wool, fiberglass, and combinations thereof. The longitudinal strips can be disposed proximate to the latent heat transfer surface at the skin-facing side of the system, whether the system is a single-use disposable system, or whether the system is a reusable system. Optionally, for a reusable system in which a portion of the system may be disposable the longitudinal strips can be disposed on either the disposable or reusable portion.

Latent Heat Delivery Surface

In specific embodiments, the latent heat delivery surface is in communication with the water vapor-air regulating portion and abuts or is adjacent to the skin surface or the skin contact layer when the system is in use. The latent heat delivery surface may contact the skin surface or alternatively be positioned with a predetermined gap between the latent heat delivery surface and the skin surface. The latent heat delivery surface may be a surface on a portion of the water vapor-air regulator portion or alternatively a separate layer. In an exemplary embodiment, the latent heat delivery surface may be, for example, a layer of material that has a basis weight of from about 20 gsm to about 100 gsm, alternatively from about 40 gsm to about 90 gsm and particularly from about 80 gsm to about 82 gsm. In an exemplary embodiment the latent heat delivery surface may have, for example, a caliper-measured thickness of from about 0.05 mm to about 12 mm, and alternatively from about 0.1 mm to about 5.0 mm, and alternatively from about 0.2 mm to about 2 mm. The latent heat surface can have an air permeability of from about 200 cm³/cm²/sec to about 500 cm³/cm²/sec, alternatively from about 300 cm³/cm²/sec to about 400 cm³/cm²/sec, and particularly about 314 cm³/cm²/sec measured using ASTM Method No. D737. The latent heat surface can have a moisture vapor transmission rate of greater than about 5,000 g/m²/24 hr measured using ASTM Method No. E96.

Non-limiting examples of suitable materials for the latent heat delivery surface include nylon, rayon, cellulose ester, polyvinyl derivatives, polyolefins, polyamides, polyesters, polypropylenes, celluloses, wool, silk, jute, hemp, cotton, linen, sisal, ramie, and combinations thereof.

Skin Contact Layer

Optionally at least one skin contact layer can be added at the skin-facing side of the system, such as at the latent heat delivery surface. Such a material has a basis weight of from about 20 gsm to about 100 gsm, alternatively from about 40 gsm to about 90 gsm and particularly from about 80 gsm to about 82 gsm. The skin contact layer has a caliper-measured thickness of from about 0.05 mm to about 12 mm, alternatively from about 0.1 mm to about 5.0 mm, and alternatively from about 0.2 mm to about 2 mm. The skin contact layer(s) can have an air permeability of from about 200 cm³/cm²/sec to about 500 cm³/cm²/sec, alternatively from about 300 cm³/cm²/sec to about 400 cm³/cm²/sec, and particularly about 314 cm³/cm²/sec measured using ASTM Method No. D737. The skin contact layer(s) can have a moisture vapor transmission rate of greater than about 5,000 g/m²/24 hr measured using ASTM Method No. E96.

Non-limiting examples of suitable materials for the skin contact layer include nylon, rayon, cellulose ester, polyvinyl derivatives, polyolefins, polyamides, polyesters, polypropylenes, celluloses, wool, silk, jute, hemp, cotton, linen, sisal, ramie, and combinations thereof.

Non-Skin Facing Side of System

In specific embodiments, it may be preferable that the exterior surface layer (i.e., non-skin facing side) of the system opposing the latent heat delivery surface and the skin-facing side (i.e. the outer side of the water vapor generating portion or surface furthest from the skin) can comprise an insulative layer that prevents the non-skin facing side of the system from becoming too hot, and that also directs heat downward toward the skin-facing side of the system. The insulative layer can be placed adjacent the opposed side of the heat cells or other water vapor source forming the water vapor generating portion.

Non-limiting examples of materials suitable for an insulative layer include, polyethylene-based foam, polypropylene-based foam, polystyrene-based foam, polyester-based foam, polyurethane-based foam, foamed plastic sheet, plastic film, foil, paper-foil laminate, non-wovens, sponge, glass wool, fiberglass, and combinations thereof.

Such an insulative layer can have a caliper-measured thickness, according to ASTM Method No. D5729, of from about 0.1 mm to about 3 mm, alternatively from about 0.5 mm to about 2.5 mm, alternatively from about 1 mm to about 2 mm, and alternatively of about 1 mm.

Such an insulative layer has an air permeability of less than about 0.025 cm³/cm²/sec measured using ASTM Method No. D737, and a moisture vapor transmission rate of less than about 250 g/m²/24 hr measured using ASTM Method No. E96. In one embodiment, the insulative layer may have a thermal conductivity of from about 0.5 W/m*K to about 285 W/m*K and a density of from about 5 kg/m³ to about 150 kg/m³. In another embodiment, the insulative layer may have a thermal conductivity of from about 0.25 W/m*K to about 0.5 W/m*K and a density of from about 5 kg/m³ to about 15 kg/m³. Thermal conductivity of this material can be obtained from the following source: "For Computer Heat-Conduction Properties data" A.L. Edwards, UCRL-505 Copyright K&K Associates 1997.

An optional one or more outermost layer of material can be added adjacent the insulative layer. Non-limiting examples of such an outermost material include those described above for skin contact layers. The insulative layer and outermost material can also be formed as a pre-combined laminate. Optionally, the one or more outermost layer of material may act as a covering and/or be a part of the structure for holding the device in place during use.

The various layers of the heat generating and/or water vapor-air regulating portion and/or latent heat delivery surface/skin contact layer can be bonded together in any number of ways known to those of skill in the art. Non-limiting examples of suitable attachment methods include heat sealing around the periphery of the layers; hot melt glue or adhesive between each layer; spray-on adhesive; ultrasonic bonding/welding; pressure bonding; crimping and combinations thereof. In certain embodiments, it may be desirable to selectively bond only some of the layers.

Moldable Portion

Optionally, the system of the present invention can also comprise a moldable portion and/or be positioned in a molded structure. The moldable portion can provide additional flexibility and stability for use of the system on portions of the body on which it may be difficult to achieve a good fit, such as the face and/or head.

Non-limiting examples of materials from which the moldable portion can be formed include metal foil, metal wire frame structure, flexible plastic structure, flexible laminate structure, and combinations thereof. Such a moldable portion can be incorporated within the structure of the system, or can be an external structure removably or non-removably attachable to an outer surface.

The wraps, packs or patches comprising moist heat systems may be self-contained or alternatively placed in a holder. A self contained embodiment may be directly attached to the user such as, for example, by an adhesive or by material extensions that form a wrap that can be secured by lapping, tying or fasteners. It should also be understood that the device may be a single use device or a reusable or partially reusable device. For reusable or partially reusable devices, replaceable parts such, as for example, the heat source should be conveniently removable, but securable into position for use.

Suitable materials for holders include, but are not limited to, materials listed as suitable for use for the latent heat delivery surface and/or exterior surface layer.

Method of Manufacture of Heat Cells

The particulate exothermic compositions of the present invention can be prepared by any known or otherwise effective technique suitable for providing an exothermic composition that provides a moist heat benefit. The particulate exothermic compositions of the present invention are preferably prepared using conventional blending techniques such as the blending technique described herein. Other suitable methods of blending the components of the particulate exothermic compositions of the present invention are more fully described in U.S. Pat. No. 4,649,895 to Yasuki et al., issued Mar. 17, 1987.

In a preferred embodiment, a particular technique of blending the components of the particulate exothermic compositions involves adding carbon to a blender or mixer, followed by adding a small amount of the total water, and then mixing the carbon/water combination. Usually enough water is added to assist in blending while avoiding premature exothermic reaction. Mixing is stopped and an absorbent gelling material is added to the carbon/water combination. Mixing is resumed until all the components are mixed thoroughly, and then iron powder is added and mixed. The composition is then blended until thoroughly mixed to form a particulate premix. Sodium chloride, optionally a hydrogen gas inhibitor such as sodium thiosulfate, and the remaining water are separately mixed to form a brine solution which is then added to the iron powder premix to form a particulate exothermic composition that is useful in the construction of a heat cell of the present invention.

In one exemplary embodiment, heat cells having two opposed surfaces can be prepared by adding a fixed amount of the particulate premix composition to a pocket in a film layer substrate sheet such as a pocket in a polypropylene/poly (ethylene-vinyl acetate)(EVA) coextruded film layer substrate sheet. In this process, water or brine is rapidly dosed on top of the premix composition, and an aerated structure such as formed of a polypropylene SMMS non-woven substrate is placed over the cell, as an opposing surface, facing the EVA film side of the preformed pocket-containing sheet. The film layer and non-woven layer are bonded together using a low heat, forming a unified structure. The resulting heat cell contains the particulate exothermic composition sealed in the pocket between the film layer and aerated structure.

It has been found that heat cells prepared by the method described herein are especially effective in providing high water vapor generation initially and throughout the desired heat treatment, provided that the heat cells comprise an exothermic composition comprising a select median particle size ratio of absorbent gelling material to iron powder defined herein.

Alternatively, individual heat cells can be prepared by using vacuum to form a pocket. That is, vacuum is used to draw the film layer substrate surface into a mold as the particulate premix composition is placed on top of the film layer substrate surface directly over the mold. The particulate premix composition drops into the vacuum formed pocket which is held in place by the vacuum exerted upon the film in the bottom of the mold. Next, a brine solution is rapidly dosed on top of the premix composition. A skin-facing aerated structure such as an SMMS polypropylene non-woven substrate surface is then placed over the first film layer substrate surface as an opposing surface, such that the particulate exothermic composition is contained between the two opposed surfaces. The particulate exothermic composition is then sealed between the first and second opposed surfaces. Once the heat cells are formed and sealed, the vacuum is released. This particular structure and method of making a plurality of heat cells is particularly advantageous for a moist heat wrap because it eliminates a need to have a separate moisture-impermeable film to keep the generated water vapor directed toward the skin-facing side of the device.

The resultant heat cells can be used individually or as a plurality of heat cells. The heat cells can be incorporated into various portable and disposable heating devices such as disposable and/or reusable skin treatment masks and/or patches. Some masks, strips, wraps, and/or patches that can include the systems can have a means for retaining the mask, strips, wraps, and/or patch in place on the skin. The retaining means can include but are not limited to, adhesives and/or fastening systems such as a re-closable two-part hook and loop fastening system, ties, fasteners, and/or an adhesive.

Alternatively, the water vapor generating portion, for example formed of a plurality of heat cells, can be disposable, and fittable into a re-usable device such that a portion of the device is disposable and a portion reusable. By way of non-limiting example, the water vapor generating portion can be disposable and the water vapor-air regulating portion can be reusable.

The resultant heat cells are packaged within 1 to 5 minutes after dosing with the brine solution in a secondary air-impermeable package to prevent the oxidation reaction from occurring until desired, as described in the aforementioned U.S. Pat. No. 4,649,895. Heat cells can also be packaged at a later time provided they are kept in an environment free from oxygen using means known to those skilled in the art such as nitrogen blanketing. Additional layers can be added or layers may be modified, as desired for various effects and performance, to the structure on the skin-facing side of the device, the opposing side, or both. Examples include, but are not limited to, a non-woven skin facing layer that can be texturized to impart softness or a layer that can be impregnated with an aroma or skin care active.

By way of non-limiting example, as described below, one or more insulative layers can be added to either the skin-facing side or the opposing side. Alternatively or in addition, various other layers can be added, as described below, to the skin-facing side of the device. The final structure can be sealed around the perimeter through all of the layers with a perimeter seal, or each layer can be sealed to adjacent layers using sealing systems, non-limiting examples of which include spray-on adhesive, ultrasonic bonding, polymer welding systems, hot melt glue or adhesive between each layer, pressure bonding, crimping, and combinations thereof.

Optional Compositions

In one exemplary embodiment the heat cells may have different heating output. For example, there may be a combination of high moist heat/short time heat cells with lower moist heat/longer time heat cells. Examples of ways in which the duration of heating of a heat cell may be controlled include, but are not limited to, the amount of exothermic particulate composition included in the cell and/or the amount of moisture available for forming water vapor. Another variation may be to use one or more moist heat delivery system thermal cells in combination with one or more conventional conduction thermal cells in a single device.

The portable moist heat delivery system of the present invention can optionally incorporate a composition to be delivered to the skin, wherein the optional composition includes aromatic compounds, non-active aromatic compounds, skin care actives, and combinations thereof.

The amounts of such actives can vary, depending on the particular active. However, in certain embodiments, the amounts provided may be less than those required for dosing the skin care active in a dry environment, such as with a dry heat mechanism or no heat mechanism.

The optional composition can be incorporated into the water vapor generating portion as a separate substrate layer, incorporated into at least one of the substrate layers forming the heat cells, incorporated into the chemistry contained in the heat cells, incorporated into separate active-containing cells, or incorporated into a separate, discrete device to be used with the water vapor generating portion and water vapor-air regulating portion. The heat cells can also comprise a separate substrate layer, or be incorporated into at least one of the opposing surfaces, a self-adhesive component and/or a sweat-absorbing component.

The moist heat delivery system is amenable to a wide variety of types of active skin care compositions including, but not limited to, volatile materials, water soluble materials, materials with limited water solubility at ambient temperatures, and combinations thereof. Further, in certain embodiments, water insoluble materials may be utilized in the system, such as, for example, when presented to the system in combination with suitable solvents and/or solubilizers.

Non-limiting examples of active aromatic compounds include menthol, camphor, eucalyptus, and mixtures thereof. Non-limiting examples of non-active aromatic compounds include benzaldehyde, citral, decanal, aldehyde, and combinations thereof.

Skin Care Compositions

A skin care composition can be applied prior to, simultaneously with, as a part of, or subsequent to application of the portable moist heat delivery system. The skin care composition can be in delivered in a variety of product forms including, but not limited to, a cream, a lotion, a gel, a foam, a paste, and/or a serum.

The skin care composition may be used as, for example, a moisturizer, a conditioner, an anti-aging treatment, a skin lightening treatment, a sunscreen, a sunless tanner, and combinations thereof. The skin care compositions may comprise a dermatologically acceptable carrier. The phrase "dermatologically-acceptable carrier", as used herein, means that the carrier is suitable for topical application to the keratinous tissue, has good aesthetic properties, is compatible with any additional components of the skin care composition, and will not cause any untoward safety or toxicity concerns. The carrier can be in a wide variety of forms. Non-limiting examples include simple solutions (water or oil based), emulsions, and solid forms (gels, sticks, flowable solids, amorphous materials). In certain embodiments, the dermatologically acceptable carrier is in the form of an emulsion. Emulsion may be generally classified as having a continuous aqueous phase (e.g., oil-in-water and water-in-oil-in-water) or a continuous oil phase (e.g., water-in-oil and oil-in-water-in-oil). The oil phase of the present invention may comprise silicone oils, non-silicone oils such as hydrocarbon oils, esters, ethers, and the like, and mixtures thereof. For example, emulsion carriers can include, but are not limited to, continuous water phase emulsions such as silicone-in-water, oil-in-water, and water-in-oil-in-water emulsion; and continuous oil phase emulsions such as water-in-oil and water-in-silicone emulsions, and oil-in-water-in-silicone emulsions.

The skin care composition may comprise a safe and effective amount of one or more skin care active ("active") useful for regulating and/or improving skin condition. "Safe and effective amount" means an amount of a compound or composition sufficient to induce a positive benefit but low enough to avoid serious side effects (i.e., provides a reasonable benefit to risk ratio within the judgment of a skilled artisan). A safe and effective amount of a skin care active can be from about $1 \times 10^{-6}\%$ to about 25% by weight of the total composition, in another embodiment from about 0.0001% to about 25% by weight of the total composition, in another embodiment from about 0.01% to about 10% by weight of the total composition, in another embodiment from about 0.1% to about 5% by weight of the total composition, in another embodiment from about 0.2% to about 2% by weight of the total composition. Suitable actives include, but are not limited to, vitamins (e.g., B3 compounds such as niacinamide, niacinnicotinic acid, tocopheryl nicotinate; B5 compounds, such as panthenol; vitamin A compounds and natural and/or synthetic analogs of Vitamin A, including retinoids, retinol, retinyl acetate, retinyl pahnitate, retinoic acid, retinaldehyde, retinyl propionate, carotenoids (pro-vitamin A); vitamin E compounds, or tocopherol, including tocopherol sorbate, tocopherol acetate; vitamin C compounds, including ascorbate, ascorbyl esters of fatty acids, and ascorbic acid derivatives such as magnesium ascorbyl phosphate and sodium ascorbyl phosphate, ascorbyl glucoside, and ascorbyl sorbate), peptides (e.g., peptides containing ten or fewer amino acids, their derivatives, isomers, and complexes with other species such as metal ions), sugar amines (e.g., N-acetyl-glucosamine), sunscreens, oil control agents, tanning actives, anti-acne actives, desquamation actives, anti-cellulite actives, chelating agents, skin lightening agents, flavonoids, protease inhibitors (e.g., hexamidine and derivatives), non-vitamin antioxidants and radical scavengers, peptides, salicylic acid, hair growth regulators, anti-wrinkle actives, anti-atrophy actives, minerals, phytosterols and/or plant hormones, tyrosinase inhibitors, N-acyl amino acid compounds, moisturizers, plant extracts, depillatories and derivatives of any of the aforementioned actives. The term "derivative" as used herein refers to structures which are not shown but which one skilled in the art would understand are variations of the basic compound. For example, removing a hydrogen atom from benzene and replacing it with a methyl group. Suitable actives are further described in U.S. Application Publication Nos. US2006/0275237A1 and US2004/0175347A1.

The skin care composition may comprise a particulate material. Particles can range from mildly abrasive polymeric microbeads to moderately abrasive materials such as sodium bicarbonate to relatively aggressive materials such as alumina crystals. Particulate materials suitable for use herein include but are not limited to bismuth oxychloride, sericite, mica, mica treated with barium sulfate or other materials, zeolite, kaolin, silica, boron nitride, lauroyl lysine, nylon, polyethylene, talc, polypropylene, polystyrene, ethylene/acrylic acid copolymer, sericite, aluminum oxide, silicone resin, barium sulfate, calcium carbonate, cellulose acetate, PTFE, polymethyl methacrylate, starch, modified starches such as aluminum starch octenyl succinate, silk, glass, fibers, ground seeds, pumice, interference pigments, and mixtures thereof.

The skin care composition may further comprise a colorant. Suitable colorants may include inorganic or organic pigments and powders. Organic pigments can include natural colorants and synthetic monomeric and polymeric colorants. Organic pigments include various aromatic types such as azo, indigoid, triphenylmethane, and anthraquinone, and xanthine dyes which are designated as D&C and FD&C blues, browns, greens, oranges, reds, yellows, etc. Organic pigments may consist of insoluble metallic salts of certified color additives, referred to as the Lakes. Inorganic pigments include iron oxides, ferric ammonium ferrocyanide, manganese violet, ultramarines, chromium, chromium hydroxide colors, and mixtures thereof. The pigments may be coated with one or more ingredients that cause the pigments to be hydrophobic. Suitable coating materials that will render the pigments more lipophilic in nature include silicones, lecithin, amino acids, phospholipids, inorganic and organic oils, polyethylene, and other polymeric materials. Suitable silicone treated pigments as disclosed in U.S. Pat. No. 5,143,722. Inorganic white or uncolored pigments include $TiO_2$, ZnO, or $ZrO_2$, which are commercially available from a number of sources. Other suitable colorants are identified in U.S. Pat. No. 7,166,279. Colorants are generally included at a weight percent such that the skin care composition yields a perceptible color. In one embodiment, the skin care composition exhibits a color that perceptibly different from the color of the applicator. By perceptibly different, refers to a difference in color that is perceptible to a person having normal sensory abilities under standard lighting conditions (e.g., natural illumination as experienced outdoors during daylight hours, the illumination of a standard 100 watt incandescent white light bulb at a distance of 2 meters, or as defined by CIE D65 standard illuminate lighting at 800 lux to a 1964 CIE standard observer).

Additionally, the skin care composition can include a depilatory for the removal of unwanted hair including, but not limited to those disclosed in U.S. Pat. Nos. 5,026,542 and 5,645,825.

Additionally, the skin care composition can include for purposes of proper formulation and stabilization anti-fungal and anti-bacterial components.

The skin care composition may also be a shaving gel or foam such as those described, for example, in U.S. Pat. Nos. 2,995,521; 3,541,581; 4,405,489; 4,528,111; 4,651,503; 5,248,495; 5,308,643; 5,326,556; and 5,500,211. Such compositions generally take the form of an oil-in-water emulsion in which the post-foaming agent, generally a volatile (i.e., low boiling point) aliphatic hydrocarbon, is solubilized in the oil phase, and the water phase comprises a water-dispersible soap, an interrupted soap component and/or a surfactant. The product is generally packaged in an aerosol container with a barrier, such as a piston or collapsible bag, to separate the post-foaming gel from the propellant required for expulsion of the product. The product is dispensed as a clear, translucent or opaque gel that is substantially free from foaming until it is spread over the skin, at which time it produces a foam lather generated by the volatilization of the volatile hydrocarbon foaming agent.

The skin care formulations can be dried down and/or dehydrated and coated onto the skin-facing side of the portable moist heat delivery system. Additionally a film could be applied to skin-facing side of the portable moist heat delivery system which when exposed to the moist heat generated by the portable moist heat delivery system is transformed into a cream or a flowable composition. One example of a composition which can be useful in the present invention is the dry film disclosed U.S. Application Publication No. 2006/0228319.

Methods of Use of the System

The present invention has many uses, non-limiting examples of which include delivering consistent, safe, efficient, and sustained moist heat to the skin. This moist heat when used in combination with a skin care active, delivers a beauty care skin benefit including, but not limited to, thickening of keratinous tissue (e.g., building the epidermis and/or dermis and/or sub-dermal layers of the skin, and where applicable the keratinous layers of the nail and hair shaft, to reduce skin, hair, or nail atrophy); increasing the convolution of the dermal-epidermal border (also known as the rete ridges); preventing loss of skin or hair elasticity, for example, due to loss, damage and/or inactivation of functional skin elastin, resulting in such conditions as elastosis, sagging, loss of skin or hair recoil from deformation; reduction in cellulite; change in coloration to the skin, hair, or nails, for example, under-eye circles, blotchiness (e.g., uneven red coloration due to, for example, rosacea), sallowness, discoloration caused by hyperpigmentation, maintaining/improving the signs of skin aging, and maintaining/improving insult-affected keratinous tissue, increasing lubricity of the skin, minimizing hair growth, removing unwanted hair and any combination thereof.

The skin benefit can be delivered by i) applying a skin care composition to the skin, and ii) applying a portable moist heat delivery system to the skin area coated with the skin care composition, and iii) activating the portable moist heat delivery system. In another embodiment the skin benefit can be delivered by i) coating the portable moist heat delivery system with a skin care composition, and ii) applying the portable moist heat delivery system to the skin area in need of treatment. In another embodiment the skin benefit can be delivered by coating the portable moist heat delivery system with a skin care composition in the form of a film, and ii) applying the portable moist heat delivery system to the skin area in need of treatment, and iii) activating the film with the moisture generated by the portable moist heat delivery system. In another embodiment the skin benefit can be delivered by i) applying the portable moist heat delivery system to the facial area, and ii) activating the portable moist heat delivery system, iii) removing the portable moist heat delivery system, and iv) shaving the skin area treated with the moist heat. The portable moist heat delivery system can be applied to the desired skin area for a period of from about twenty seconds to about eight (8) hours, alternatively from about twenty minutes to about four (4) hours, alternatively from about one (1) minute to about sixty (60) minutes, alternatively from about fifteen (15) minutes to about thirty (30) minutes, alternatively from about one (1) minute to about twenty (20) minutes, alternatively from about twenty (20) minutes to about forty (40) minutes and alternatively from about one half (½) hour to about two (2) hours.

Because the temperature of the water vapor-air mixture of the system in use on a body is only a few degrees above normal skin temperature of from about 32° C. to about 35° C., and the dew point temperature of the water vapor-air mixture is approximately that of normal skin temperature when it reaches the skin, heat can be safely transferred to the skin via latent heat of condensation of water from the water vapor-air mixture. Thus, the system is able to safely deliver a large amount of heat to the skin, wherein from about 15% to about 95%, alternatively from about 20% to about 80% and alternatively from about 40% to about 75% of the heat is delivered as latent heat. In one embodiment, the moist heat system delivers about 15% to about 95% of the heat as latent heat of condensation for at least 10 minutes, alternatively, at least 30 minutes, or at least 1 hour, in certain embodiments at least 3 hours, or alternatively at least 5 hours.

In addition to delivering moist heat, the moist heat system may also provide moisturization to the skin as the water vapor condenses to water and delivers the latent heat of condensation to the skin.

Skin surface temperature is measured by the following method. All measurements are made at ambient conditions. The temperature range during the measurements is 21° C.-23° C. Relative humidity range is 38%-42%. Temperature measurements may be made using a thermocouple. The thermocouple may be positioned between the hair and the latent heat delivery surface and/or hair contact layer. In one embodiment, the temperature measurements are made with K-type thermocouples (Omega, part # 5SRTC-TT-K-40-72) and recorded by temperature data logger (Omega, HH84). To measure the temperature of the surface of a user's skin, the user sits in a room at about 22° C. for about 20 minutes to normalize the skin to the room temperature and conditions. During that time, a thermocouple is placed and taped on the skin surface, taking care that the tape is not placed over the sensing area of the thermocouple. Upon expiration of the equilibration time, temperature can be measured and recorded for a desired period of time.

If the effect of a system of the present invention on the skin surface temperature is measured, each system of the present invention to be measured is constructed then sealed in an impermeable container and set aside for 24 hours to equilibrate before testing. When a system is to be tested, it is removed from a protective package and placed on a skin surface, on top of the thermocouple. Skin temperature is measured before application of the system, and recorded for 60 minutes after application of the system and initiation of heating.

The temperature of the water vapor-air mixture delivered to the skin surface can also be measured by placing thermocouples on a user's skin. Skin temperature is measured before application of the system, and is recorded for 60 minutes after application of the system and initiation of heating.

The dew point temperature is preferably measured when the moist heat system is activated and in position on a user as the dew point temperature of particular interest is related to the amount of water vapor between the user and the moist heat system. The amount of water vapor between the body and the moist heat wrap is dependent on the amount of water vapor generated by the device minus the amount of water vapor condensed and the amount of water vapor that flows out of the device. The dew point may be measured, for example with a HUMICAP® HMT337 dew point transmitter with Stainless Steel HM47453P filter, available from Vaisala, Woburn Mass., USA.

In one embodiment, the system of the present invention as described herein can generate and deliver from about 75 W/m$^2$ to about 500 W/m$^2$, alternatively from about 100 W/m$^2$ to about 200 W/m$^2$, alternatively from about 200 W/m$^2$ to about 500 W/m$^2$, and alternatively from about 300 W/m$^2$ to about 500 W/m$^2$ of heat flux at a safe skin and/or hair temperature. In another embodiment, the system of the present invention as described herein can generate and deliver from about 180 W/m$^2$ to about 500 W/m$^2$, alternatively from about 200 W/m$^2$ to about 500 W/m$^2$, and alternatively from about 220 W/m$^2$ to about 300 W/m$^2$ of heat flux at a safe skin temperature.

The system generates and delivers heat to a surface of the skin wherein from about 15% to about 95%, alternatively from about 20% to about 80%, and about 40% to about 75% of the heat delivered to a surface of the skin is delivered as latent heat upon condensation of the water vapor-air mixture. Without wishing to be held by any theory, it is believed that the remainder of the heat transferred to the skin may be heat transferred by conduction. Because a majority of the heat transfer is through condensation on the body, through control of the dew point temperature by water vapor-air mixing, the system of the present invention can deliver peak heating levels to the body of up to two to five times that of a conventional dry heating wrap while maintaining constant skin temperature of about 43° C. or less, thereby providing a safe usage experience for the user.

The system of the present invention also generates from about 0.05 mg water vapor/min/cm$^2$ to about 2.5 mg water vapor/min/cm$^2$ of water vapor generating portion, and alternatively from about 0.1 mg water vapor/min/cm$^2$ to about 2.0 mg water vapor/min/cm$^2$ of water vapor generating portion, wherein the water vapor delivers moisture to the surface of the skin via condensation onto the surface of the skin.

The amount of water vapor generated, and water vapor generation rate can be measured by measuring the weight change of a system of the present invention, or other exothermic heating device, from before initiation of heating to after the system is spent, and over time during use of the system. To measure and record the weight change, a Mettler-Toledo Balance Model PG503-S is connected to a computer running Software Wedge v3.0C—Professional software using a RS232C interface cable. Prior to testing the balance is calibrated according to the manufacturer's instructions. A 1.59 mm (1/16 inch) thick polystyrene foam sheet is placed on top of the scale of the balance and the balance is zeroed.

The system to be tested is removed from an air-tight foil pouch where it is stored after manufacture, and is placed in the center of the polystyrene foam sheet. To begin the test, simultaneously "menu" on the balance and "start/stop" on a stop watch function on the computer are pressed. Using the stopwatch as a reference, "menu" is pressed on the balance once every minute to log the weight of the system being tested into the software. The starting weight of the exothermic heating device and the weight of the exothermic heating device thereafter are recorded until the system is spent, and thereby moisture loss from the start to the end of the reaction can be measured.

The amount of weight loss is correlated to the amount of water loss, which estimates the amount of water vapor generated during the reaction. With an exothermic composition such as that of the present invention, because none of the other components of the exothermic composition is lost during the reaction, and water is not consumed as part of the reaction, weight lost can be correlated to water lost and water vapor generated. Measurements based on weight lost, and calculations of water vapor generated are approximations because during the course of the reaction iron oxide is produced, and thus some weight is also gained during the course of the reaction. However, a minimal amount of iron oxide is produced and thus a de minimus amount of weight is gained. Therefore, the amount of weight lost approximates the amount of water lost.

Amount of water vapor generated per area of skin of a user can be calculated by dividing the total amount of water vapor generated by the system by the area of skin to which a system is applied. Water vapor generated per unit time can also be calculated by dividing the amount of water vapor generated by a system by the duration of water vapor generation. One of ordinary skill in the art would understand how to perform such calculations, either manually or using computer software.

In addition, the system can increase skin moisture level by at least about 300% versus skin moisture level prior to application of the system, over a time period of less than about 30 minutes.

Amount of skin moisture and increase in skin moisture is measured with a Corneometer 810 capacitance skin moisture meter (Courage Khazaka Electronics, Cologne, Del.). The corneometer determines the humidity level of the stratum corneum of the skin by electrical capacitance. Alteration in skin hydration level results in a change in capacitance. The capacitance probe is applied to the skin for one second at a pressure of 7.1 N/cm$^2$. The degree of skin capacitance is indicated from 1-100 units. One unit represents a water content of the stratum corneum of 0.02 mg/cm$^2$ at a measuring depth of 20 nm. Very dry skin is less than 30 units, dry skin is 30-45 units and sufficiently moisturized skin is greater than 45 units.

Tissue (i.e. skin in this case) capacitance is measured by applying electromagnetic waves at a frequency of 100,000 cycles/second (Hz), to a depth of 20 nm, to image the skin surface. The probe is placed on the skin of a test subject at a location desired to be studied. Prior to testing, the subject sits in a room at about 22° C. and 40% relative humidity for 20 minutes, to allow the skin to come to a normalized condition. Capacitance, from which skin moisture is calculated, is measured before and immediately after removal of the heating modality.

A kit can be made including a combination of one or more of the aforementioned skin care compositions and a portable moist heat delivery system.

EXAMPLES

Portable Moist Heat Delivery System Examples

Examples 1-3 Water Vapor Source

The water vapor source exemplified below is exothermic heat cells filled with a particulate exothermic composition for use in the water vapor generating portion of the system of the present invention.

The particulate exothermic compositions exemplified below are prepared by using conventional blending techniques to form the particulate exothermic compositions, wherein the resultant compositions provide for the construction of heat cells of the present invention.

A pre-mix is prepared by adding activated carbon and water into a blender or mixer such as a Littleford Day Mixer, and mixing for about ten minutes. A polyacrylate absorbent gelling material is then added, and the mixture is mixed for about 10 minutes. Next, sponge iron powder is added to the mixer, and the resultant pre-mix is mixed for about 5 minutes.

Approximately 2.2 g of the resultant pre-mix composition are added to each preformed pocket, which pockets have been created with a vacuum to form the pockets, in a sheet of polypropylene/EVA coextruded film.

Next, a brine solution is prepared by adding water, sodium chloride, and optionally sodium thiosulfate into a mixer and mixing for about fifteen minutes. The resultant brine solution is then rapidly dosed onto the pre-mix composition.

An aerated skin-facing surface of polypropylene SMMS non-woven material is placed over the pockets containing the pre-mix and brine, facing the EVA side of the preformed pocket-containing film sheet. The film sheet and SMMS are bonded together using a low heat, forming a unified structure. The resulting unified structure contains heat cells containing the particulate exothermic composition sealed in the pockets between the opposing surfaces of the aerated surface and the opposed film layer surface.

The cells begin to generate heat shortly after the brine is added to the particulate composition, therefore the top and bottom surfaces are bonded and the finished heat cells are quickly packaged in an air tight secondary packaging for future use. Table 1 illustrates different particulate exothermic compositions of heat cells of the present invention.

TABLE 1

Particulate Exothermic Compositions

| Component | Composition 1 (Wt. %) | Composition 2 (Wt. %) | Composition 3 (Wt. %) |
|---|---|---|---|
| Iron powder | 60.40 | 56.75 | 58.70 |
| Activated Carbon | 4.05 | 3.81 | 3.94 |
| Absorbent Gelling Material | 5.09 | 4.78 | 4.94 |
| Sodium Chloride | 3.02 | 3.47 | 1.38 |
| Sodium Thiosulfate | 0.38 | 0.43 | — |
| Water | 27.06 | 30.76 | 31.04 |

Example embodiments of the present invention are described below with reference to the Figures. The same symbols represent the same structural elements throughout.

Figure 3:
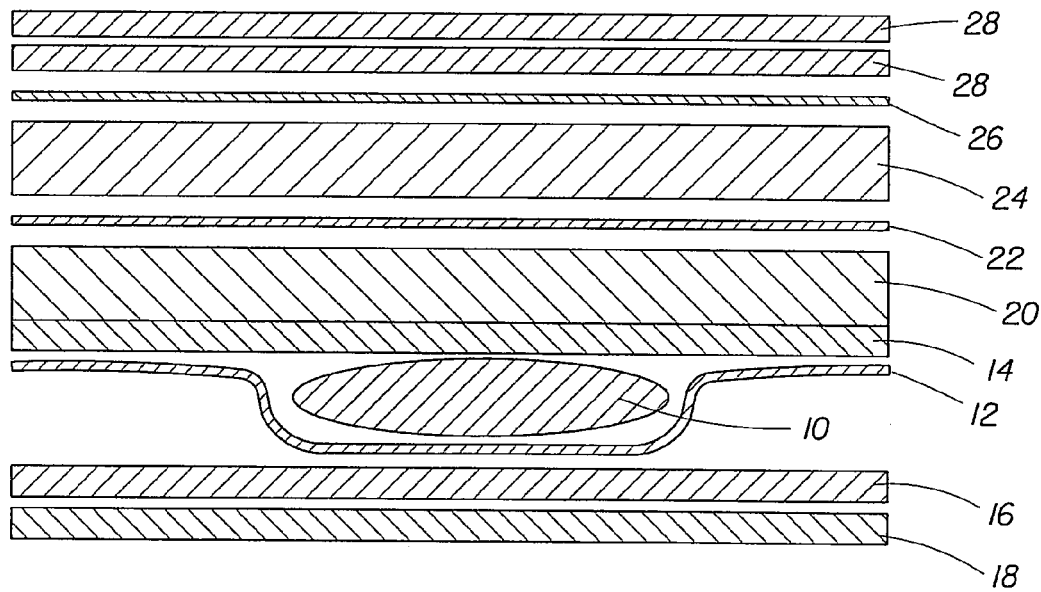
FIG. 3 is a schematic diagram of an embodiment of the present invention.

FIG. 3 illustrates an embodiment having two water vapor-air mixing layers and two water vapor-air distribution layers as part of a water vapor-air regulating portion. Heat cells are constructed according to Example 1 using Composition 1 above. Adjacent to the aerated skin-facing surface of the heat cell is a water vapor-air regulating portion constructed as follows. Adjacent to the opposed surface of the heat cells is an insulative layer and an outermost layer.

The heat cells have a particulate exothermic composition 10 dosed in a pocket formed in an opposed surface 12 of non-air permeable, non-moisture permeable polypropylene/EVA film layer opposing a polypropylene SMMS aerated skin-facing surface 14.

Attached to the opposed surface 12 is a 1.59 mm (1/16 inch) insulative polypropylene foam layer 16. Attached to foam layer 16 is an outermost polypropylene non-woven layer 18.

Adjacent the aerated skin-facing surface 14 is a 3 mm thick first water vapor-air mixing layer 20 of high loft polyethylene/polyester non-woven batting. Adjacent the first water vapor-air mixing layer 20 is a first water vapor-air distribution layer 22 of 1.59 mm (1/16 inch) thick perforated polypropylene foam. Adjacent the first water vapor-air distribution layer 22 is a second 3 mm thick water vapor-air mixing layer 24 of high loft polyethylene/polyester non-woven batting. Adjacent the second water vapor-air mixing layer 24 is a second water vapor-air distribution layer 26 of 1.59 mm (1/16 inch) thick perforated polypropylene foam. Attached to the second water vapor-air distribution layer 26 are two skin-contact layers of polypropylene non-woven material 28. The layers are sealed together around the periphery of the layers to form a system.

Figure 4:
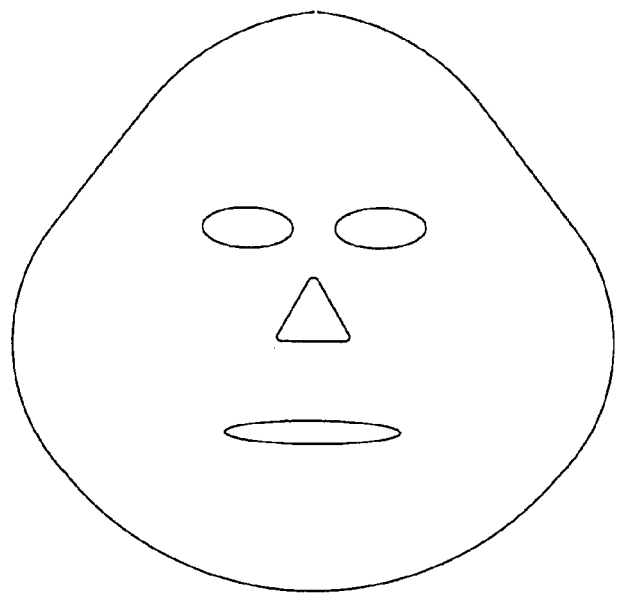
FIG. 4 is a schematic diagram of an embodiment of the present invention.
Figure 5:
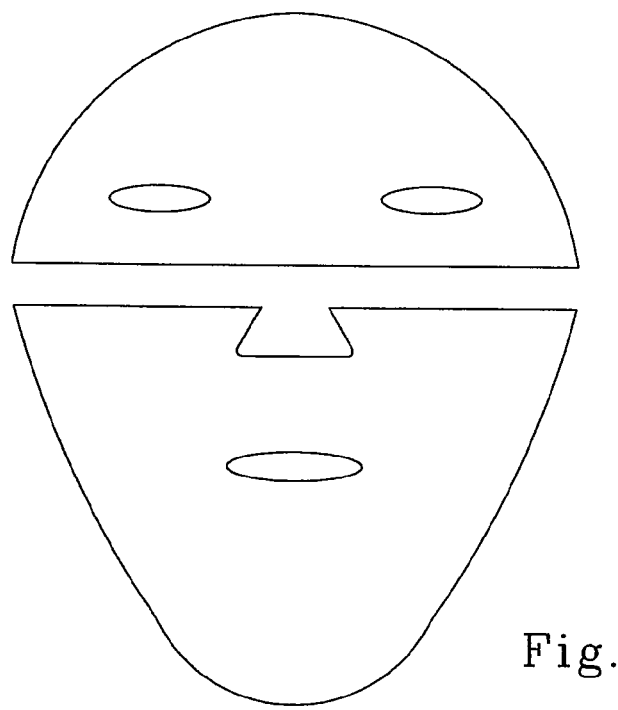
FIG. 5 is a schematic diagram of an embodiment of the present invention.

FIG. 4 illustrates an embodiment of the invention wherein the portable moist heat delivery system is face mask shaped. The mask can be a single piece (as shown in FIG. 4) or multiple pieces, as shown in FIG. 5.

Figure 6:
FIG. 6 is a schematic diagram of an embodiment of the present invention.

FIG. 6 illustrates an embodiment of the invention wherein the portable moist heat delivery system is a rectangular shape which can be used to apply to portions of the face such as the upper lip and/or the forehead.

Figure 7:
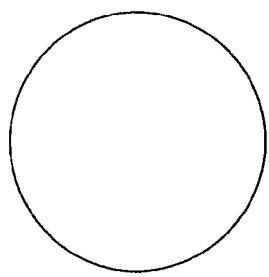
FIG. 7 is a schematic diagram of an embodiment of the present invention.

FIG. 7 illustrates an embodiment of the invention wherein the portable moist heat delivery system is a circular shape which can be used to apply to portions of the face.

Figure 8:
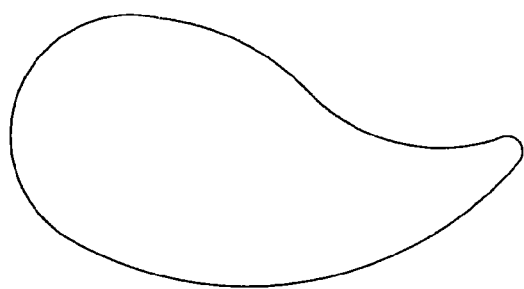
FIG. 8 is a schematic diagram of an embodiment of the present invention.

FIG. 8 illustrates an embodiment of the invention wherein the portable moist heat delivery system is shaped to fit to cover the skin surrounding the corners of the eyes.

Figure 9:
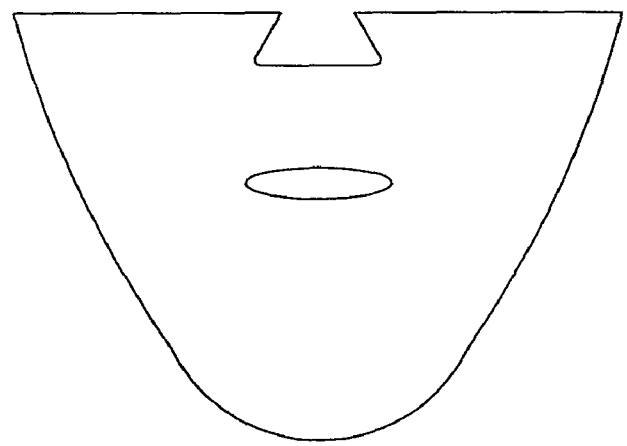
FIG. 9 is a schematic diagram of an embodiment of the present invention.

FIG. 9 illustrates an embodiment of the invention wherein the portable moist heat delivery system is shaped to fit the lower half of the face. This embodiment can be useful for preparing the lower half of the face for shaving.

Figure 10:
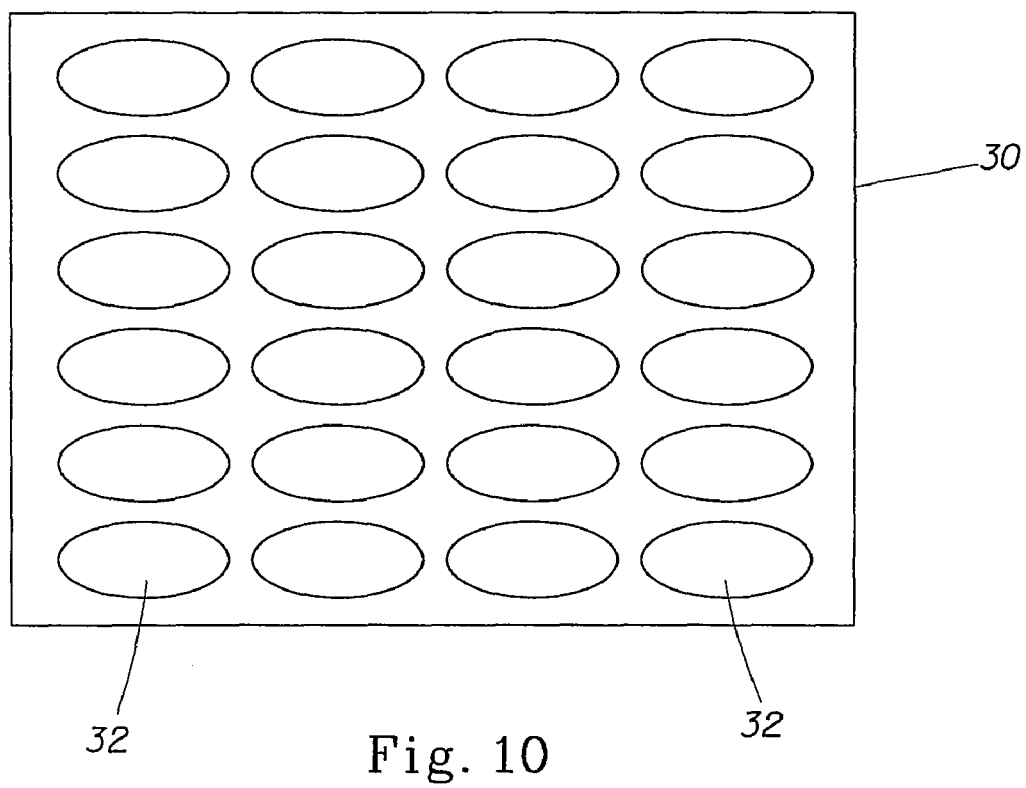
FIG. 10 is a schematic diagram of an embodiment of the present invention.

FIG. 10 is a top plan view of an embodiment of the present invention 30 having twenty-four (24) heat cells 32 each comprising a water vapor source and together forming a water vapor generating portion.

Examples of Skin Care Compositions

The following formulations are non-limiting examples of suitable skin care compositions that provide one or more of the above mentioned readily perceptible differences. Where applicable, ingredients are given in CTFA name. While particular embodiments of the subject invention have been described, it will be obvious to those skilled in the art that various changes and modifications to the subject invention can be made without departing from the spirit and scope of the invention. The Examples may be slightly modified by omitting key components that provide for the readily perceptible difference (e.g., Example 5 contains colorants FD&C Red 40 and Blue 1 which could be omitted to yield a colorant free examples). Specifically, one or more of components listed in boldface may be omitted to yield alternate examples.

|  | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| PHASE A |  |  |  |  |  |  |  |  |  |  |
| DC-9040 *1 | 5.10 | 13.5 |  | 50.7 |  |  |  |  |  |  |
| DC-9045 *2 |  |  | 15 |  | 32.75 | 14.0 |  | 14.0 |  |  |
| PEG-4 |  |  |  |  |  |  |  |  | q.s to 100 |  |
| Dimethicone | 4.10 |  | 6 |  |  | 5.2 |  | 5.2 |  |  |
| Polymethyl silsesquioxane *3 | 4.10 | 7.5 |  |  |  |  | 0.5 |  |  | 0.5 |
| Polyethylene beads *4 |  |  |  |  |  |  |  | 2.0 | 2.0 |  |
| Cyclomethicone | 11.40 | 23.5 | 15 |  | 10.0 | 1.05 |  | 1.05 |  |  |
| KSG-210 *5 | 5.40 | 2.5 |  |  |  |  |  |  |  |  |
| KSG-310 *6 |  |  |  | 20.0 |  |  |  |  |  |  |
| Polyethylene wax *7 | 2.05 |  |  |  |  |  |  |  |  |  |
| DC-2503 Cosmetic Wax *8 | 3.77 |  |  |  | 1.5 |  |  |  |  |  |
| Abil EM97 *9 |  | 0.45 |  |  | 0.45 |  |  |  |  |  |
| KF 6017 *10 |  | 0.375 |  |  |  |  |  |  |  |  |
| Cetyl Ricinoleate |  | 0.25 |  |  |  |  |  |  |  |  |
| KTZ Fine TiO$_2$ coated Mica *11 | 1.00 |  |  |  |  |  |  |  |  |  |
| Dow Corning 1503 *12 |  |  | 3 |  |  | 3.5 |  | 3.5 |  |  |
| Octisalate |  |  |  | 4.0 |  |  |  |  |  |  |
| Homosalate |  |  |  | 4.0 |  |  |  |  |  |  |
| Octocrylene |  |  |  | 1.5 |  |  |  |  |  |  |
| Avobenzene |  |  |  | 2.0 |  |  |  |  |  |  |
| Isopropyl Lauroylsarcosinate |  |  |  | 7.5 |  |  |  |  |  |  |
| Tospearl 145A *13 |  |  |  | 10 |  |  |  |  |  |  |
| Prestige Fire Red 11S2 *14 |  |  |  | 0.1 |  |  |  |  |  |  |
| Microthene FN-510 *15 |  |  | 9 |  |  | 10.0 |  | 10.0 |  |  |
| Petrolatum |  |  |  |  | 0.5 |  |  |  |  |  |
| Isohexadecane |  |  |  |  |  |  | 3.0 |  |  | 3.0 |
| Isopropyl Isostearate |  |  |  |  |  |  | 1.0 |  |  | 1.0 |
| Stearic Acid |  |  |  |  |  |  | 0.4 |  |  | 0.4 |
| Cetearyl Glucoside |  |  |  |  |  |  | 0.2 |  | 0.5 | 0.2 |
| Cetyl Alcohol |  |  |  |  |  |  | 1.0 |  | 1.3 | 1.0 |
| Stearyl Alcohol |  |  |  |  |  |  |  |  | 20.0 |  |
| Magnesium Sulfate Anhydrous |  |  |  |  |  |  |  |  | 3.0 |  |
| PEG/PEG-300/55 Copolymer |  |  |  |  |  |  |  |  | 2.0 |  |
| TegoCare CP *16 |  |  |  |  |  |  |  |  | 1.78 |  |
| Econol TM-22 *17 |  |  |  |  |  |  |  |  | 0.80 |  |
| Distearyldimonium chloride |  |  |  |  |  |  |  |  | 0.25 |  |
| Hydroxypropyl cellulose |  |  |  |  |  |  |  |  |  |  |

|  | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Petrolatum |  |  |  |  | 0.5 |  |  |  | 0.15 |  |
| Fragrance | 0.10 |  |  | 0.2 |  |  |  |  |  |  |
| PHASE B |  |  |  |  |  |  |  |  |  |  |
| Glycerin | 10.00 | 10.00 | 11 |  | 10 | 10.0 | 2.0 | 10.0 |  | 2.0 |
| Panthenol | 0.5 | 1.00 | 0.7 |  | 1.0 | 1.0 |  | 1.0 |  |  |
| Pentylene Glycol | 3.00 |  |  |  |  |  |  |  |  |  |
| Propylene Glycol |  | 1.00 |  |  | 1.0 | 1.0 |  | 1.0 |  |  |
| Butylene Glycol |  | 1.00 |  |  | 1.0 | 1.0 |  | 1.0 |  |  |
| Tocopherol Acetate |  | 0.50 | 0.2 |  | 0.5 | 0.5 | 0.5 | 0.5 |  | 0.5 |
| N-Acetyl Glucosamine | 0.50 |  | 2.0 |  |  |  |  |  |  |  |
| Hexamidine Diisethanoate *18 | 0.10 |  |  |  |  |  |  |  |  |  |
| Niacinamide | 5.00 | 4.00 | 5.00 |  | 5 | 5.0 | 2.5 | 5.0 |  | 2.5 |
| Methylparaben | 0.20 | 0.10 |  |  | 0.1 |  |  |  |  |  |
| Ethylparaben | 0.05 | 0.10 |  |  | 0.1 | 0.1 |  | 0.1 |  |  |
| Benzyl Alcohol | 0.25 | 0.50 |  |  | 0.4 | 0.4 |  | 0.4 | 0.1 |  |
| Propyl Paraben |  | 0.10 |  |  |  | 0.1 |  | 0.1 |  |  |
| Disodium EDTA |  | 0.10 | 0.05 |  | 0.1 |  | 0.1 |  |  | 0.1 |
| Polysorbate 20 |  |  | 0.6 |  |  | 0.8 |  | 0.8 |  |  |
| Glydant Plus Liquid *19 |  |  | 0.3 |  |  |  |  |  |  |  |
| Laureth-4 |  |  | 0.2 |  |  | 0.2 |  | 0.2 |  |  |
| Sucrose Polycottonseedate |  |  |  |  | 0.5 |  |  |  |  |  |
| Allantoin |  |  |  |  | 0.1 | 0.2 |  | 0.2 |  |  |
| Prodew 400 *20 |  |  |  |  |  |  |  |  |  |  |
| GLW75CAP-MP *21 |  |  |  |  |  | 0.35 |  | 0.35 |  |  |
| Hydrolyzed wheat protein |  |  |  |  |  |  | 2.0 |  |  |  |
| Menthol |  |  |  |  |  |  |  |  |  | 0.5 |
| Vanillyl alcohol isoamyl ether monophosphate |  |  |  |  |  |  |  |  |  | 0.05 |
| Sodium Chloride | 0.50 |  |  |  |  |  |  |  |  |  |
| FD&C Red No. 40 |  |  |  |  | .00025 |  |  |  |  |  |
| FD&C Blue 1 |  |  |  |  | .00011 |  |  |  |  |  |
| Water | q.s to 100 | q.s to 100 | q.s to 100 |  | q.s to 100 | q.s to 100 | q.s to 100 | q.s to 100 |  | q.s to 100 |
| Thickener |  |  |  |  |  |  |  |  |  |  |
| Sepigel 305 *22 |  |  | 1.6 |  |  | 1.5 | 1.5 | 1.5 |  | 1.5 |

(Values are wt %)
*1 12.5% Dimethicone Crosspolymer in Cyclopentasiloxane. Available from Dow Corning.
*2 Dimethicone Crosspolymer in Cyclopentasiloxane. Available from Dow Corning.
*3 E.g., Tospearl 145A or Tospearl 2000. Available from GE Toshiba Silicone
*4 PFM (250-500 μm) colored beads from Kobo.
*5 25% Dimethicone PEG-10/15 Crosspolymer in Dimethicone. Available from Shin-Etsu
*6 PEG-15/Lauryl Dimethicone Crosspolymer in Mineral Oil from Shin-Etsu.
*7 Jeenate 3H polyethylene wax. Available from Jeen
*8 Stearyl Dimethicone. Available from Dow Corning.
*9 Bis-PEG/PPG-14/14 Dimethicone. Available from Degussa
*10 PEG-10 Dimethicone. Available from Shin-Etsu.
*11 Hydrophobically modified $TiO_2$ coated Mica. Available from Kobo.
*12 Dimethicone/Dimethiconol blend from Dow Corning.
*13 Polymethylsilsesquioxane from General Electric.
*14 Mica and iron oxides from Eckart.
*15 Polyethylene powder available from Equistar.
*16 Dioleoylethyl hydroxyethylmonium methosulfate mixture available from Degussa Care & Surface Specialties, Hopewell, VA.
*17 Behenyltrimethylammonium chloride in carrier available from Sanyo Performance Chemicals, JP.
*18 Hexamidine diisethionate, available from Laboratoires Serobiologiques.
*19 DMDM Hydantoin and Iodopropynyl Butylcarbamate blend available from Lonza, Inc.
*20 Available from Ajinomoto U.S.A., Inc., Paramus NJ.
*21 $TiO_2$ with water, glycerine, polyacrylate, and methylparaben available from Kobo Products.
*22 Polyacrylamide, $C_{13}$-$C_{14}$ Isoparaffin, and Laureth-7 blend from Seppic.

For example 1, combine the ingredients of Phase A in a suitable container. In a separate suitable container, combine the ingredients of Phase B. Heat each phase to 75-80° C. while mixing each phase using a suitable mixer (e.g., Anchor blade, propeller blade) until each reaches temperature and is homogenous. Slowly add Phase B to Phase A while continuing to mix Phase A. Continue mixing until batch is uniform. Homogenize product with Ultra-Turrax homogenizer (IKA, Inc) or equivalent and pour product into suitable containers at 75-80° C. Store the containers at room temperature without disturbing for at least 12 hours.

For examples 2 and 5, in a suitable container, combine the ingredients of Phase A and mix with a suitable mixer until homogenous. In a separate container, combine the ingredients of Phase B and mix until homogenous. Slowly add Phase B to Phase A while continuing to mix Phase A. Continue mixing until batch is uniform. Homogenize product with Ultra-Turrax homogenizer (IKA, Inc) or equivalent and pour product into suitable containers.

For examples 3, 6-8, and 10, in a suitable vessel, the water phase ingredients are combined and mixed until uniform; the water phase may be warmed to dissolve all ingredients. In a separate suitable container, the silicone/oil phase ingredients are combined and mixed until uniform; the silicone/oil phase may be warmed to dissolve all ingredients. Half the thickener and then the silicone/oil phase is added to the water phase and the resulting emulsion is milled (e.g., with a Tekmar T-25). The remainder of the thickener and then the remaining ingredients are then added to the emulsion while stirring. Once the composition is uniform, the product is poured into suitable containers.

For examples 4 and 9, in a suitable vessel, the ingredients are combined and mixed until uniform; the composition may be warmed to dissolve all ingredients. Once the composition is uniform, the product is poured into suitable containers.

Examples of Post-Foaming Shave Gel

|  | Weight Percent | | | | |
| --- | --- | --- | --- | --- | --- |
| Ingredient | Ex. 1 | Ex. 2 | Ex. 3 | Ex. 4 | Ex. 5 |
| Water | 78.24 | 75.02 | 75.94 | 75.55 | 75.64 |
| Triethanolamine | 5.88 | 5.88 | 5.88 | 5.88 | 5.88 |
| Palmitic acid | 7.53 | 7.53 | 7.53 | 7.53 | 7.53 |
| Stearic acid | 2.53 | 2.53 | 2.53 | 2.53 | 2.53 |
| Glyceryl Oleate | 1.94 | 1.94 | 1.94 | 1.94 | 1.94 |
| PEG-23M | 0.05 | 0.05 | 0.05 | 0.05 | 0.05 |
| PEG-90M |  | 0.06 | 0.06 | 0.06 | 0.06 |
| Hydroxyethylcellulose | 0.49 | 0.49 | 0.49 | 0.49 | 0.49 |
| Lubrajel ® oil* | 0.49 | 0.97 | 0.49 | 0.97 | 0.49 |
| Sorbitol |  | 0.97 | 0.97 | 0.97 | 0.97 |
| Glycerin |  | 0.49 |  |  | 0.49 |
| PTFE powder |  | 0.15 | 0.15 | 0.15 | 0.15 |
| Fragrance |  | 0.87 | 0.78 | 0.78 | 0.78 |
| Colorant |  | 0.10 | 0.29 | 0.19 | 0.10 |
| Other (e.g. Vit. E, Aloe, etc.) |  | 0.10 | 0.05 | 0.06 | 0.05 |
| Isopentane/isobutane (3:1) | 2.85 | 2.85 | 2.85 | 2.85 | 2.85 |

*Lubrajel oil contains 1.0%-1.3% Glyceryl Acrylate/Acrylic Acid Copolymer (MW ≅ 1 million)

The above-described compositions are made in the following manner: The water soluble polymers (polyethylene oxide, hydroxyethylcellulose) are added to water and mixed until the polymers are completely dissolved (about 30 min.). The aqueous mixture is then heated and the glyceryl oleate, sorbitol and fatty acids are added at about 60° C. and well mixed while the heating continues. At 80-85° C. the triethanolamine is added and mixed for about 20 minutes to form the aqueous soap phase. After cooling the aqueous soap phase to room temperature, the remaining components (i.e., Lubrajel® oil, glycerin, fragrance, colorant, botanicals) are added to the aqueous soap phase and mixed well to form the gel concentrate. (Water may be added if required to bring the batch weight to 100%, thereby compensating for any water loss due to evaporation.) The concentrate is then combined with the volatile post-foaming agent under pressure within the filling line and filled into bottom-gassed aerosol cans with shearing through the valve under nitrogen pressure. (Note: if, instead of Lubrajel® oil, a different hydrogel-forming polymer is utilized, it is preferred to pre-hydrate the polymer in water prior to inclusion in the formulation.)

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of providing benefits to the skin comprising:
    (a) applying a skin care composition to the skin to provide a beauty care benefit;
    (b) applying a portable moist heat delivery system to the skin coated with the skin care composition, the portable moist heat delivery system comprising:
        (1) a water vapor generating portion comprising a water vapor source and a heat source; and
        (2) a water vapor-air regulating portion located at a skin-facing side of the water vapor generating portion, the water vapor-air regulating portion comprising a water vapor-air mixing layer, a water vapor-air distribution layer, and optionally a skin contact layer;
        the water vapor generating portion and the water vapor-air regulating portion being in fluid communication; and the water vapor-air regulating portion having a latent heat delivery surface disposed adjacent the water vapor-air regulating portion, where the water vapor-air regulating portion provides a mixture of water vapor and air having a water vapor to dry air ratio of less than 0.065 kg water/kg dry air, wherein the portable moist heat delivery system transfers from about 15% to about 95% of heat to a user as latent heat of condensation, while maintaining skin temperature less than 43° C.; and
    (c) activating the portable moist heat delivery system.

2. The method of claim 1, wherein the skin care composition comprises a skin care active selected from the group consisting of vitamins, peptides, sugar amines, sunscreens, oil control agents, tanning actives, anti-acne actives, desquamation actives, anti-cellulite actives, chelating agents, skin lightening agents, flavonoids, protease inhibitors, non-vitamin antioxidants and radical scavengers, hair growth regulators, anti-wrinkle actives, anti-atrophy actives, minerals, phytosterols and/or plant hormones, tyrosinase inhibitors, N-acyl amino acid compounds, moisturizers, plant extracts, depillatories and any combination thereof.

3. The method of claim 1, wherein the portable moist heat delivery system is left on the skin for about 1 minute to about eight hours.

4. The method of claim 3, wherein the portable moist heat delivery system is left on the skin for about 15 minutes.

5. The method of claim 3, wherein the portable moist heat delivery system is left on the skin for about 30 minutes.

6. The method of claim 1 wherein the portable moist heat delivery system transfers from about 20% to about 80% of heat to a user as latent heat of condensation, while maintaining skin temperature less than 43° C.

7. The method of claim 1 wherein the portable moist heat delivery system transfers from about 40% to about 75% of heat to a user as latent heat of condensation, while maintaining skin temperature less than 43° C.

8. The method of claim 1 wherein the portable moist heat delivery system is mask shaped.

9. The method of claim 8 wherein the skin care composition is a film on the portable moist heat delivery system.

10. The method of claim 1 wherein the portable moist heat delivery system is a rectangular patch.

11. The method of claim 1 wherein the portable moist heat delivery system further comprises an adhesive.

12. The method of claim 1 wherein the portable moist heat delivery system is a circular patch.

13. The method of claim 1 wherein the portable moist heat delivery system is shaped to cover the lower half of the face.

14. The method of claim 1 further comprising the step of providing a skin surface temperature of at least 36° C. within about 5 minutes of initiation of heating of the portable moist heat delivery system.

15. The method of claim 1 wherein the water vapor source comprises at least one water vapor generating heat cell.

16. A method of providing benefits to the skin comprising:
   (a) applying a portable moist heat delivery system to the facial skin, wherein the portable moist heat delivery system comprises:
      (1) a water vapor generating portion comprising a water vapor source and a heat source; and
      (2) a water vapor-air regulating portion located at a skin-facing side of the water vapor generating portion, the water vapor-air regulating portion comprising a water vapor-air mixing layer, a water vapor-air distribution layer, and optionally a skin contact layer; the water vapor generating portion and the water vapor-air regulating portion being in fluid communication and the water vapor-air regulating portion having a latent heat delivery surface disposed adjacent the water vapor-air regulating portion; where the water vapor-air regulating portion provides a mixture of water vapor and air having a water vapor to dry air ratio of less than 0.065 kg water/kg dry air, and wherein the portable moist heat delivery system transfers from about 15% to about 95% of heat to a user as latent heat of condensation, while maintaining skin temperature less than 43° C.;
   (b) applying a shaving composition to the facial skin; and
   (c) shaving the facial skin.

17. The method of claim 16, wherein the portable moist heat delivery system is applied to the facial skin for 5 minutes.

18. The method of claim 1, further comprising:
   (d) contacting the skin with the mixture of water vapor and air having a water vapor to dry air ratio of less than 0.065 kg water/kg dry air; condensing the mixture of water vapor and air at the latent heat delivery surface to transfer the latent heat energy to the skin; or a combination thereof.

19. The method of claim 16, further comprising:
contacting the skin with the mixture of water vapor and air having a water vapor to dry air ratio of less than 0.065 kg water/kg dry air; condensing the mixture of water vapor and air at the latent heat delivery surface to transfer the latent heat energy to the skin; or a combination thereof.

20. The method of claim 1, further comprising:
   (d) transferring from about 15% to about 95% of heat to a user as latent heat of condensation.

21. The method of claim 16, further comprising:
transferring from about 15% to about 95% of heat to a user as latent heat of condensation.

* * * * *